United States Patent
Crowther et al.

(10) Patent No.: US 10,968,290 B2
(45) Date of Patent: Apr. 6, 2021

(54) METALLOCENE-CATALYZED POLYALPHA-OLEFINS

(71) Applicant: ExxonMobil Chemical Patents Inc., Baytown, TX (US)

(72) Inventors: Donna J. Crowther, Blairsville, GA (US); Patrick C. Chen, Houston, TX (US); Jacqueline A. Lovell, Crosby, TX (US); Md Safatul Islam, Pearland, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 15/921,757

(22) Filed: Mar. 15, 2018

(65) Prior Publication Data

US 2018/0282443 A1 Oct. 4, 2018

Related U.S. Application Data

(60) Provisional application No. 62/477,683, filed on Mar. 28, 2017.

(51) Int. Cl.
| | | |
|---|---|---|
| *C10M 107/02* | (2006.01) | |
| *C07C 2/22* | (2006.01) | |
| *C08F 4/6592* | (2006.01) | |
| *C08F 210/16* | (2006.01) | |
| *C08F 10/14* | (2006.01) | |
| *B01J 31/38* | (2006.01) | |
| *C08F 10/08* | (2006.01) | |
| *C08F 110/14* | (2006.01) | |
| *B01J 31/22* | (2006.01) | |
| *C08F 4/659* | (2006.01) | |

(52) U.S. Cl.
CPC .......... *C08F 4/65927* (2013.01); *B01J 31/38* (2013.01); *C07C 2/22* (2013.01); *C08F 10/08* (2013.01); *C08F 10/14* (2013.01); *C08F 110/14* (2013.01); *C08F 210/16* (2013.01); *C10M 107/02* (2013.01); *B01J 31/2295* (2013.01); *B01J 2231/12* (2013.01); *B01J 2531/46* (2013.01); *B01J 2531/48* (2013.01); *B01J 2531/49* (2013.01); *C08F 4/659* (2013.01); *C08F 4/65908* (2013.01); *C08F 4/65912* (2013.01); *C08F 2500/15* (2013.01); *C08F 2500/16* (2013.01)

(58) Field of Classification Search
CPC .............................. C10M 107/02; C07C 2/22
See application file for complete search history.

(56) References Cited

U.S. PATENT DOCUMENTS

| | | |
|---|---|---|
| 3,367,987 A | 2/1968 | Walsh |
| 4,658,078 A | 4/1987 | Slaugh et al. |
| 4,874,880 A | 10/1989 | Miya et al. |
| 4,973,788 A | 11/1990 | Lin et al. |
| 5,087,788 A | 2/1992 | Wu |
| 5,286,823 A | 2/1994 | Rath |
| 5,605,219 A | 2/1997 | Aulbach et al. |
| 5,625,105 A | 4/1997 | Lin et al. |
| 5,688,887 A | 11/1997 | Bagheri et al. |
| 5,741,868 A | 4/1998 | Winter et al. |
| 5,919,983 A | 7/1999 | Rosen et al. |
| 6,043,401 A | 3/2000 | Bagheri et al. |
| 6,403,732 B2 | 6/2002 | Marks et al. |
| 6,479,722 B1 | 11/2002 | De Wet et al. |
| 6,548,723 B2 | 4/2003 | Bagheri et al. |
| 6,548,724 B2 | 4/2003 | Bagheri et al. |
| 6,818,585 B2 | 11/2004 | Crowther et al. |

(Continued)

FOREIGN PATENT DOCUMENTS

| | | |
|---|---|---|
| CN | 105622807 | 6/2016 |
| EP | 1 026 177 A | 8/2000 |

(Continued)

OTHER PUBLICATIONS

Antinolo, A., et al. Reactivity of Zirconium Complexes Incorporating Asymmetrically Substituted ansa Ligands and Their Use as Catalysts in Olefin Polymerization. X-Ray Crystal Structures of [Me2Si(n5-C5Me4)(n5-C5H3R)]ZrCl2(R=Et, iPr), Organometallics, vol. 21, No. 12, pp. 2460-2467, 2002.

Fan, W., et al. "Alternating Stereospecific Copolymerization of Ethylene and Propylene with Metallocene Catalysts", Journal of American Chemical Society, vol. 123, pp. 9555-9563, 2001.

(Continued)

*Primary Examiner* — Caixia Lu

(57) ABSTRACT

Unsaturated and hydrogenated polyalpha-olefin products can be made with a high selectivity toward vinylidenes and tri-substituted vinylenes combined, a high selectivity toward vinylidenes, and a low selectivity toward 1,2-di-substituted vinylenes by using a catalyst system comprising a metallocene compound having the following structure in the polymerization reaction:

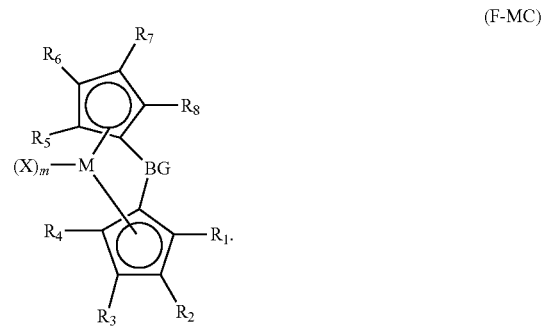

(F-MC)

19 Claims, No Drawings

(56) References Cited

U.S. PATENT DOCUMENTS

| | | | |
|---|---|---|---|
| 7,087,602 B2 | 8/2006 | Thomas et al. | |
| 7,101,940 B2 | 9/2006 | Schottek et al. | |
| 7,129,197 B2 | 10/2006 | Song et al. | |
| 7,199,072 B2 | 4/2007 | Crowther et al. | |
| 7,214,745 B2 | 5/2007 | Arai et al. | |
| 7,799,879 B2 | 9/2010 | Crowther et al. | |
| 7,989,670 B2 | 8/2011 | Wu et al. | |
| 8,207,390 B2* | 6/2012 | Wu .................. | C08F 10/14 585/523 |
| 8,318,998 B2 | 11/2012 | Crowther et al. | |
| 8,399,724 B2 | 3/2013 | Crowther et al. | |
| 8,426,659 B2 | 4/2013 | Holtcamp et al. | |
| 8,501,894 B2 | 8/2013 | Crowther et al. | |
| 8,513,478 B2 | 8/2013 | Wu et al. | |
| 8,530,712 B2 | 9/2013 | Wu et al. | |
| 8,580,902 B2 | 11/2013 | Crowther et al. | |
| 8,623,974 B2 | 1/2014 | Jiang et al. | |
| 8,642,497 B2 | 2/2014 | Berris | |
| 8,669,326 B2 | 3/2014 | Hagadorn et al. | |
| 8,669,330 B2 | 3/2014 | Stewart | |
| 8,748,361 B2 | 6/2014 | Wu et al. | |
| 8,754,170 B2 | 6/2014 | Hagadorn et al. | |
| 8,816,027 B2 | 8/2014 | Crowther et al. | |
| 8,835,563 B2 | 9/2014 | Crowther et al. | |
| 8,940,839 B2 | 1/2015 | Hagadorn et al. | |
| 9,365,788 B2 | 6/2016 | Emett et al. | |
| 9,409,834 B2 | 8/2016 | Wu et al. | |
| 9,688,792 B2 | 6/2017 | Welle et al. | |
| 10,040,884 B2* | 8/2018 | Harada ............... | C10M 177/00 |
| 2002/0010077 A1 | 1/2002 | Lue et al. | |
| 2002/0062011 A1 | 5/2002 | Campbell, Jr. et al. | |
| 2003/0105251 A1 | 6/2003 | Crowther et al. | |
| 2004/0102590 A1 | 5/2004 | McCullough et al. | |
| 2005/0159299 A1 | 7/2005 | Rodriguez et al. | |
| 2008/0177121 A1* | 7/2008 | Wu .................. | C08F 10/00 585/530 |
| 2009/0318644 A1 | 12/2009 | Brant et al. | |
| 2010/0038290 A1 | 2/2010 | Wang et al. | |
| 2011/0160502 A1* | 6/2011 | Wu .................. | C08F 10/00 585/16 |
| 2013/0023633 A1 | 1/2013 | Holtcamp et al. | |
| 2013/0303818 A1 | 11/2013 | Inagaki et al. | |
| 2014/0194277 A1 | 7/2014 | Ishihama et al. | |
| 2015/0203602 A1 | 7/2015 | Sun et al. | |
| 2017/0114166 A1* | 4/2017 | Harada ............... | C10M 177/00 |
| 2017/0233516 A1 | 8/2017 | Yang et al. | |
| 2018/0037521 A1 | 2/2018 | Islam et al. | |
| 2018/0094088 A1 | 4/2018 | Crowther et al. | |
| 2018/0146444 A1 | 5/2018 | Chen et al. | |
| 2019/0135961 A1 | 5/2019 | Joung et al. | |
| 2019/0248936 A1 | 8/2019 | Yang et al. | |
| 2019/0263942 A1 | 8/2019 | Jeong et al. | |
| 2019/0330392 A1 | 10/2019 | Faler et al. | |

FOREIGN PATENT DOCUMENTS

| | | |
|---|---|---|
| EP | 0 856 518 B | 4/2003 |
| EP | 1 900 744 A | 3/2008 |
| EP | 1 614 699 B | 10/2008 |
| JP | 2005-336092 | 12/2005 |
| JP | 2011-037164 | 2/2011 |
| WO | 1995/027717 | 10/1995 |
| WO | 99/60032 | 11/1999 |
| WO | 99/67347 A | 12/1999 |
| WO | 2007/022244 A | 2/2007 |
| WO | 2009/155471 | 12/2009 |
| WO | 2010/014344 | 2/2010 |
| WO | 2012/134720 | 10/2012 |
| WO | 2013/055483 A | 4/2013 |
| WO | 2018/182982 | 10/2018 |
| WO | 2018/182984 | 10/2018 |

OTHER PUBLICATIONS

Alonso-Moreno, C., "Novel Indenylzirconium Complexes as Supported Catalysts in the Polymerization of Ethylene", European Journal of Inorganic Chemical, vol. 2005, 2924-2934, 2005.

Gomez-Ruiz, S., et al. "Synthesis and Catalytic Applications of C1 Symmetric Group 4 ansa-metallocene Complexes", Journal of Molecular Catalysis A: Chemical, vol. 264, No. 1-2, pp. 260-269, 2007.

Lee, M.H., et al., "Ethylene-Bridged Pseudo-Cs Symmetric ansa-zirconocene Complexes: Synthesis, Structures and Propylene Polymerization Behavior", Journal of Organometallic Chemistry, vol. 561, No. 1-2, pp. 37-47, 1998.

Villasenor, E., et al., "Neutral Dimethylzirconocene Complexes as Initiators for the Ring-Opening Polymerization of [epsilon]-Caprolactone", European Journal of Inorganic Chemistry, 1184-1196, 2013.

Hanna, T.E., et al., "Diazene Dehydrogenation Follows H 2 Addition to Coordinated Dinitrogen in an ansa-Zirconocene Complex", Inorganic Chemistry, vol. 46, No. 5, pp. 1675-1683, 2007.

Antinolo, A., et al., "New Group 4 Metallocene and Niobocene Complexes Containing Phosphane-Functionalized ansa-Ligands" European Journal of Inorganic Chemistiy-Chemische Berichte, pp. 2470-2476, 2002.

Alonso-Moreno, C., et al., Niobium, Titanium, Zirconium and Hafnium Complexes Incorporating Germanium Bridged ansa Ligands. X-Ray Crystal Structures of [Zr[Me2Ge(n5-C5Me4)2]Cl2] and [Me2Ge(n5-C5Me4)(n5-C5H4)]Cl2](M=Zr,Hr), Journal of Organometailic Chemistry, vol. 656, No. 1-2, pp. 129-138, 2002.

Antinolo, A., et al., Synthesis and Reactivity of Alkylzirconium Complexes Incorporating Asymmetrically Substituted ansa Ligands-X-Ray Crystal Structure of [Zr{Me2Si([n5-C5Me4)([n5-C5H3Me)} (CH2Ph)Cl], European Journal of Inorganic Chemistry, pp. 2626-2632, 2003.

Gomez-Ruiz, S., et al. "Synthesis, Characterization and Catalytic Behaviour of ansa-zirconocene Complexes Containing Tetraphenylcyclopentadienyl rings: X-Ray Crystal Structures of [Zr{Me2Si(n5-C5Ph4)(n5-C5H3R)}Cl2](R=H, But)", Journal of Organometallic Chemistry, vol. 693, No. 4, pp. 601-610, 2007.

Obora, Y., et al., "Ancillary Ligand Effects in Chiral C1-Symmetric ansa-Metallocene Catalyst for Stereoregular alpha.-Olefin Polymerization. "Wingspan" Modification with Octahydrofluorene", Organometallics, vol. 16, No. 12, pp. 2503-2505, 1997.

Gomez-Ruiz, S., et al., "Study of the Cytotoxic Activity of Alkenyl-Substituted ansa-titanocene Complexes", Inorganic Chemistry Communications, vol. 10, No. 7, pp. 748-752, 2007.

Gomez-Ruiz, S., et al., Synthesis, Characterization and Applications in Ethylene Polymerization of Asymmetric ansa-titanocene Complexes. Molecular Structure of [T1{Me2Si(n5-C5Me4)(n5-C5H3iPr)}Cl2], Inorganica Chimica Acta, vol. 362, No. 4, pp. 1042-1046, 2009.

Kaminsky, W., et al. "Crystal Structure and Propene Polymerization Characteristics of Bridged Zirconocene Catalysts", Journal of Organometallic Chemistry, vol. 497, pp. 181-193, 1995.

Rulhoff, S., et al. "Synthesis and Characterization of Defined Branched Poly(propylene)s with Different Microstructures by Copolymerization of Propylene and Linear Ethylene Oligomers ($C_n$=26-28) with Metallocenes/MAO Catalysts," *Macromolecules*, v.207, pp. 1450-1460, 2006.

Kaneyoshi, H., et al. "Synthesis of Block and Graft Copolymers with Linear Polyethylene Segments by Combination of Degenerative Transfer Coordination Polymerization and Atom Transfer Radical Polymerization," *Macromolecules*, v.38(13), pp. 5425-5435, 2005.

Teuben, J., et al. "Catalytic Olefin Oligomerization and Polymerization with Cationic Group IV Metal Complexes [Cp2MMe (THT)] + [BPh4]–, M=Ti, Zr and Hf", *J. Mol. Catal.*, v.62(3), pp. 277-287; 1990.

Yang, X., et al. "Cationic Metallocene Polymerization Catalysts. Synthesis and Properties of the First Base-Free Zirconocene Hydride" *Angew. Chem., Int'l Edn.*, Engl., v.31, No. 10, pp. 1375-1377, 1992.

Small, B. L., et al "Polymerization of Propylene by a New Generation of Iron Catalysts: Mechanisms of Chain Initiation, Propagation, and Termination", *Macromol.*, v.32, pp. 2120-2130, 1999.

(56) References Cited

OTHER PUBLICATIONS

Weng, W., et al. "Synthesis of vinyl-terminated isotactic poly(propylene)", *Macromol Rapid Comm.*, v.21, pp. 1103-1107, 2000.

Markel, E. J., et al. "Metallocene-Based Branch-Block Thermoplastic Elastomers", *Macromolecules*, v.33, pp. 8541-8548, 2000.

Moscardi, G., et al. "Propene Polymerization with the Isospecific, Highly Regioselective rac-Me$_2$C(3-t-Bu-1-Ind)$_2$ZrCl$_2$/MAO Catalyst. 2. Combined DFT/MM Analysis of Chain Propagation and Chain Release Reactions", *Organometallics*, v. 20, pp. 1918, 2001.

Zhu, S., et al. "Copolymerization of Propylene with Poly(ethylene-co-propylene) Macromonomer and Branch Chain-Length Dependence of Rheological Properties" *Macromol.*, v.35, pp. 10062-10070, 2002.

Zhu, S., et al. "Synthesis and Characterization of Long-Chain-Branched Polyolefins with Metallocene Catalysts: Copolymerization of Ethylene with Poly(ethylene-co-propylene) Macromonomer", *Macromol. Rap. Commun.*, v.24, pp. 311-315, 2003.

Coates, G. W., et al. "Synthesis of Allyl-Terminated Syndiotactic Polypropylene: Macromonomers for the Synthesis of Branched Polyolefins", *Macromolecules*, v.38, pp. 6259-6268, 2005.

Rose, J. M., et al. "Poly(ethylene-co-propylene macromonomer)s: Synthesis and Evidence for Starlike Conformations in Dilute Solution", *Macromolecules*, v.41, pp. 559-567, 2008.

Janiak, C., et al. "Metallocene Catalysts for Olefin Oligomerization", *Macromol. Symp.*, v.236, pp. 14-22, 2006.

Abu-Omar, M. M., "Highly Regioselective α-Olefin Dimerization Using Zirconium and Hafnium Amine Bis(phenolate) Complexes", *Organometallics*, v.36 (15), pp. 2934-2939, 2017.

Bazan, G. C., et al. "(Phenylboratabenzene)zirconium Complexes: Tuning the Reactivity of an Olefin Polymerization Catalyst", *Organometallics*, v.16, pp. 2492-2494, 1997.

Chemical Abstract Service (CAS) Registry No. 909721-53-5.
Chemical Abstract Service (CAS) Registry No. 943521-08-2.
U.S. Appl. No. 62/885,103, filed Aug. 9, 2019.
U.S. Appl. No. 62/629,200, filed Feb. 12, 2018.
U.S. Appl. No. 62/732,311, filed Sep. 17, 2018.
U.S. Appl. No. 62/662,972, filed Apr. 26, 2018.
U.S. Appl. No. 62/769,208, filed Nov. 19, 2018.

* cited by examiner

METALLOCENE-CATALYZED POLYALPHA-OLEFINS

CROSS-REFERENCE OF RELATED APPLICATIONS

This application claims the benefit of Provisional Application No. 62/477,683, filed Mar. 28, 2017, the disclosures of which is incorporated herein by reference.

FIELD OF THE INVENTION

The present disclosure relates to polyalpha-olefin ("PAO") materials and processes for making the same. In particular, the present disclosure relates to ethylenically unsaturated PAO materials and saturated PAO materials derived from polymerization of alpha-olefins in the presence of a catalyst system comprising a metallocene-compound.

BACKGROUND OF THE INVENTION

Oligomeric, ethylenically unsaturated molecules made from the polymerization of alpha-olefins are known. For example, U.S. Pat. No. 8,748,361 B2 discloses a mixture comprising unsaturated polyalpha-olefin ("uPAO") material made from, e.g., oligomerization of alpha-olefins in the presence of metallocene catalysts. It was disclosed in this reference that the uPAOs could comprise, among others, vinyls, vinylenes, 1,2-di-substituted vinylenes, and tri-substituted vinylenes. The vinyls and vinylidenes are terminal olefins, while the di- and tri-substituted vinylene olefins are internal olefins.

In U.S. Pat. No. 8,748,361 B2, mixtures of the uPAOs produced from the polymerization step were subsequently hydrogenated by hydrogen using a hydrogenation catalyst. A great majority of the C=C double bonds in the mixture were then hydrogenated to form a substantially saturated, stable, aliphatic PAO mixture which, in turn, can be separated by distillation to obtain a hydrogenated PAO material that is particularly suitable as the base stock for lubricating oil compositions used in various applications. To the extent the presence of C=C bonds in the PAO molecules in a lubricating oil composition is considered generally detrimental to the performance of the oil, especially to the oxidation stability thereof, it is highly desired that the uPAO has an overall composition that would result in saturation of the C=C bonds at a degree as high as possible in the hydrogenation step.

Recently, however, research and development in various chemical fields reveal that the ethylenically unsaturated PAO materials prepared from oligomerization of linear alpha-olefins can be particularly advantageously used as an intermediate for making various specialty chemicals because of the reactivity of the C=C double bond present in molecular structure of the oligomer molecules. For example, various chemical functional groups can be bonded to the carbon backbone of the uPAO molecule when a chemical agent reactive with the C=C bond is allowed to contact the uPAO material. The functional group thus introduced onto the PAO structure can bring about unique properties to the functionalized and saturated PAO molecules.

It has been found that the reactivity of the C=C bonds in vinyls, vinylidenes, 1,2-di-substituted vinylenes and tri-substituted vinylenes are different with regard to many chemical functionalization agents. For a specific type of functionalization agent, one or more particular type(s) of olefin(s) may be more desirable than the other(s). In addition, uPAOs having various molecular weight and molecular weight distribution and differing reactivities may be desired for making differing derivatives comprising differing functional groups thereon. It is known that vinylidenes and tri-substituted vinylenes are more reactive than 1,2-di-substituted vinylenes with many common reagents reactive with C=C double bonds.

U.S. Publication No. 2013/0023633 A1 discloses metallocene compounds and use thereof in making polyolefins rich in vinyls.

There remains a need for uPAO materials having a high concentration of vinylidenes and tri-substituted vinylenes and a low concentration of 1,2-di-substituted vinylenes and processes for making such uPAO materials.

SUMMARY OF THE INVENTION

It has been found that by using a catalyst system comprising a metallocene compounds with certain specific substituted ligands described in detailed below, high selectivity toward vinylenes and tri-substituted vinylenes combined, high selectivity toward vinylidenes, and low selectivity toward 1,2-di-subtituted vinylenes can be achieved in alpha-olefin polymerization reactions. An unsaturated PAO product rich in vinylenes, rich in vinylidenes and tri-substituted vinylenes combined, and low in 1,2-di-substituted vinylenes can be made from the polymerization reaction mixture.

Thus, a first aspect of the present invention relates to process for making a polyalpha-olefin ("PAO"), the process comprising:

contacting a C4-C30 alpha-olefin feed with a catalyst system comprising a metallocene compound in a polymerization reactor under polymerization conditions to effect a polymerization reaction to obtain a polymerization reaction mixture comprising vinylidenes, tri-substituted vinylenes, optionally 1,2-di-substituted vinylenes, and optionally vinyls; and obtaining an unsaturated PAO product from the polymerization reaction mixture, wherein the unsaturated PAO product comprises vinylidenes, tri-substituted vinylenes, optionally 1,2-di-substituted vinylenes, optionally vinyls, and substantially free of the alpha-olefin feed, wherein:
the metallocene compound has a structure represented by formula (F-MC) below comprising a first cyclopentadienyl ring directly connected with $R^1$, $R^2$, $R^3$, and $R^4$ and a second cyclopentadienyl ring directly connected with $R^5$, $R^6$, $R^7$, and $R^8$:

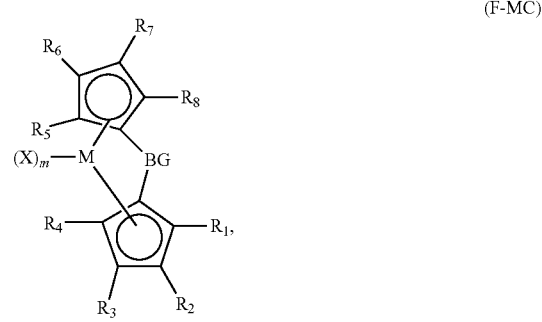

(F-MC)

wherein:
$R^1$ and $R^4$ are each independently a hydrogen, a substituted or unsubstituted linear, branched linear, or cyclic C1-C30 hydrocarbyl group, $R^2$ and $R^3$ are each independently a substituted or unsubstituted linear, branched linear, or cyclic C1-C50 hydrocarbyl group, or alternatively, two or more of $R^1$, $R^2$, $R^3$, and $R^4$, taken together, with the carbon atoms in the first cyclopentadienyl ring to which they are directly connected, form one or more substituted or unsubstituted ring annelated to the first cyclopentadienyl ring;

$R^5$, $R^6$, $R^7$, and $R^8$ are each independently hydrogen, or a substituted or unsubstituted linear, branched linear, or cyclic C1-C30 hydrocarbyl group, provided $R^6$ and $R^7$ are not both hydrogen; or alternatively, two or more of $R^5$, $R^6$, $R^7$, and $R^8$, taken together, with the intermediate carbon atoms in the second cyclopentadienyl ring to which they are directly connected, form one or more substituted or unsubstituted ring annelated to the second cyclopentadienyl ring;

provided: the first cyclopentadienyl ring and the second cyclopentadienyl ring are not annelated to ring structures simultaneously;

BG is a bridging group connected directly with both the first cyclopentadienyl ring and the second cyclopentadienyl ring;

M is a transition metal;

X, the same or different at each occurrence, is independently selected from halogens, C1-C50 substituted or unsubstituted linear, branched, or cyclic hydrocarbyl groups; and m is an integer equal to v-2, where v is the valency of M.

A second aspect of the present invention relates to an unsaturated PAO product comprising, based on the total moles of all vinyls, vinylidenes, 1,2-di-substituted vinylenes, and tri-substituted vinylenes contained therein: at least 40 mol % of vinylidenes and tri-substituted vinylenes combined; 0.1 to 10 mol % of 1,2-di-substituted vinylenes; and 0 to 40 mol % of vinyls.

A third aspect of the present invention relates to the unsaturated PAO product obtainable from the process according to the first aspect of the present invention.

A fourth aspect of the present invention relates to a saturated PAO product that is obtainable by contacting the unsaturated PAO product of the second or third aspect with hydrogen in the presence of a hydrogenation catalyst.

A fifth aspect of the present invention relates to lubricating oil base stocks containing the unsaturated or saturated PAO products of any of the preceding aspects of the present invention.

DETAILED DESCRIPTION OF THE INVENTION

The term "alkyl" or "alkyl group" interchangeably refers to a saturated hydrocarbyl group consisting of carbon and hydrogen atoms. An alkyl group can be linear, branched linear, cyclic, or substituted cyclic.

The term "cycloalkyl" or "cycloalkyl group" interchangeably refers to a saturated hydrocarbyl group wherein the carbon atoms form one or more ring structures.

The term "alkenyl" or "alkenyl group" interchangeably refers to a linear unsaturated hydrocarbyl group comprising a C=C bond therein.

The term "cycloalkenyl" or "cycloalkenyl group" interchangeably refers to cyclic hydrocarbyl group comprising a C=C bond in the ring.

The term "aryl" or "aryl group" interchangeably refers to a hydrocarbyl group comprising an aromatic ring structure therein.

The term "hydrocarbyl group" or "hydrocarbyl" interchangeably refers to a group consisting of hydrogen and carbon atoms only. A hydrocarbyl group can be saturated or unsaturated, linear or branched linear, cyclic or acyclic, aromatic or non-aromatic.

As used herein, a substituted group means such a group in which at least one atom is replaced by a different atom or a group. Thus a substituted alkyl group can be an alkyl group in which at least one hydrogen atom is replaced by a hydrocarbyl group, a halogen, any other non-hydrogen group, and/or a least one carbon atom and hydrogen atoms bonded thereto is replaced by a different group.

The term "Cn" group or compound refers to a group or a compound comprising carbon atoms at total number thereof of n. Thus, a "Cm-Cn" group or compound refers to a group or compound comprising carbon atoms at a total number thereof in the range from m to n. Thus, a C1-C50 alkyl group refers to an alkyl group comprising carbon atoms at a total number thereof in the range from 1 to 50.

The term "carbon backbone" refers to the longest straight carbon chain in the molecule of the compound or the group in question. "Branches" refer to any non-hydrogen group connected to the carbon backbone.

The term "olefin" refers to an unsaturated hydrocarbon compound having a hydrocarbon chain containing at least one carbon-to-carbon double bond in the structure thereof, wherein the carbon-to-carbon double bond does not constitute a part of an aromatic ring. The olefin may be linear, branched linear, or cyclic. "Olefin" is intended to embrace all structural isomeric forms of olefins, unless it is specified to mean a single isomer or the context clearly indicates otherwise.

The term "alpha-olefin" refer to an olefin having a terminal carbon-to-carbon double bond in the structure thereof ($(R^1R^2)$—C=$CH_2$, where $R^1$ and $R^2$ can be independently hydrogen or any hydrocarbyl group, preferably $R^1$ is hydrogen, and $R^2$ is an alkyl group). A "linear alpha-olefin" is an alpha-olefin defined in this paragraph wherein $R^1$ is hydrogen, and $R^2$ is hydrogen or a linear alkyl group.

The term "vinyl" means an olefin having the following formula:

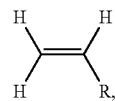

wherein R is a hydrocarbyl group, preferably a saturated hydrocarbyl group such as an alkyl group.

The term "vinylidene" means an olefin having the following formula:

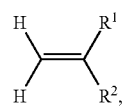

wherein $R^1$ and $R^2$ are each independently a hydrocarbyl group, preferably a saturated hydrocarbyl group such as alkyl group.

The term "1,2-di-substituted vinylene" means
(i) an olefin having the following formula:

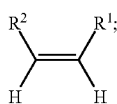

or
(ii) an olefin having the following formula:

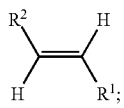

or
(iii) a mixture of (i) and (ii) at any proportion thereof,
wherein $R^1$ and $R^2$, the same or different at each occurrence, are each independently a hydrocarbyl group, preferably saturated hydrocarbyl group such as alkyl group.

The term "tri-substituted vinylene" means an olefin having the following formula:

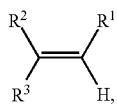

wherein $R^1$, $R^2$, and $R^3$ are each independently a hydrocarbyl group, preferably a saturated hydrocarbyl group such as alkyl group.

As used herein, "polyalpha-olefin(s)" ("PAO(s)") includes any oligomer(s) and polymer(s) of one or more alpha-olefin monomer(s). PAOs are oligomeric or polymeric molecules produced from the polymerization reactions of alpha-olefin monomer molecules in the presence of a catalyst system, optionally further hydrogenated to remove residual carbon-carbon double bonds therein. Thus, the PAO can be a dimer, a trimer, a tetramer, or any other oligomer or polymer comprising two or more structure units derived from one or more alpha-olefin monomer(s). The PAO molecule can be highly regio-regular, such that the bulk material exhibits an isotacticity, or a syndiotacticity when measured by $^{13}C$ NMR. The PAO molecule can be highly regio-irregular, such that the bulk material is substantially atactic when measured by $^{13}C$ NMR. A PAO material made by using a metallocene-based catalyst system is typically called a metallocene-PAO ("mPAO"), and a PAO material made by using traditional non-metallocene-based catalysts (e.g., Lewis acids, supported chromium oxide, and the like) is typically called a conventional PAO ("cPAO").

As used herein, the term "carbon backbone" of a PAO molecule is defined as the straight carbon chain therein having the largest number of carbon atoms.

As used herein, the term "pendant group" with respect to a PAO molecule refers to any group other than hydrogen attached to the carbon backbone other than those attached to the carbon atoms at the very ends of the carbon backbone.

As used herein, the term "length" of a pendant group is defined as the total number of carbon atoms in the longest carbon chain in the pendant group, counting from the first carbon atom attached to the carbon backbone. The pendant group may contain a cyclic group or a portion thereof in the longest carbon chain, in which case half of the carbon atoms in the cyclic group are counted toward the length of the pendant group. Thus, by way of examples, a linear C8 pendant group has a length of 8; the pendant groups PG-1 (cyclohexylmethylene) and PG-2 (phenylmethylene) each has a length of 4; and the pendant groups PG-3 (o-heptylphenylmethylene) and PG-4 (p-heptylphenylmethylene) each has a length of 11. Where a PAO molecule contains multiple pendant groups, the arithmetic average of the lengths of all such pendant groups are calculated as the average length of the all pendant groups in the PAO molecule.

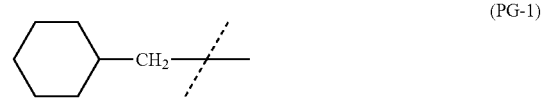
(PG-1)

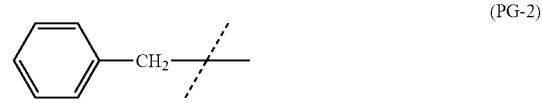
(PG-2)

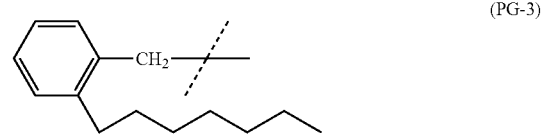
(PG-3)

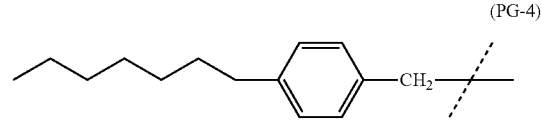
(PG-4)

In the present disclosure, cyclopentadiene and cyclopentadienyl are abbreviated as Cp.

In the present disclosure, any metallocene compound may have one or more optical isomers. All metallocene compound identified herein by name or structure shall include all possible optical isomers thereof and mixtures of any such optical isomers. For example, metallocene compound $Me_2Si(Me_4Cp)(3\text{-}Prind)ZrMe_2$ shall include the following two optical isomers and mixtures thereof, even if only one structure is given when it is described:

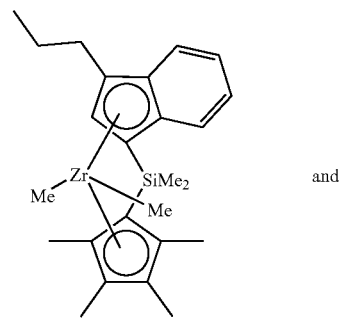 and

-continued

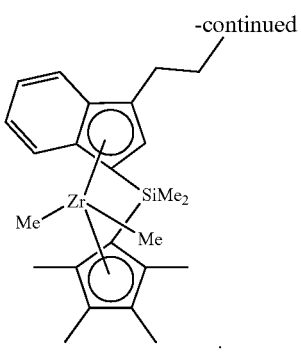

Unless specified otherwise, the term "substantially all" with respect to PAO molecules means at least 90 mol % (such as at least 95 mol %, at least 98 mol %, at least 99 mol %, or even 100 mol %).

Unless specified otherwise, the term "substantially free of" with respect to a particular component means the concentration of that component in the relevant composition is no greater than 10 mol % (such as no greater than 5 mol %, no greater than 3 mol %, or no greater than 1 mol %), based on the total quantity of the relevant composition.

As used herein, a "lubricant" refers to a substance that can be introduced between two or more moving surfaces and lower the level of friction between two adjacent surfaces moving relative to each other. A lubricant "base stock" is a material, typically a fluid at the operating temperature of the lubricant, used to formulate a lubricant by admixing it with other components. Non-limiting examples of base stocks suitable in lubricants include API Group I, Group II, Group III, Group IV, Group V and Group VI base stocks. Fluids derived from Fischer-Tropsch process or Gas-to-Liquid ("GTL") processes are examples of synthetic base stocks useful for making modern lubricants. GTL base stocks and processes for making them can be found in, e.g., WO 2005/121280 A1 and U.S. Pat. Nos. 7,344,631; 6,846,778; 7,241,375; 7,053,254.

All kinematic viscosity values in the present disclosure are as determined according to ASTM D445. Kinematic viscosity at 100° C. is reported herein as KV100, and kinematic viscosity at 40° C. is reported herein as KV40. Unit of all KV100 and KV40 values herein is cSt, unless otherwise specified.

All viscosity index ("VI") values in the present disclosure are as determined according to ASTM D2270.

All Noack volatility ("NV") values in the present disclosure are as determined according to ASTM D5800 unless specified otherwise. Unit of all NV values is wt %, unless otherwise specified.

All numerical values within the detailed description and the claims herein are modified by "about" or "approximately" the indicated value, and take into account experimental error and variations that would be expected by a person having ordinary skill in the art.

In the present disclosure, all percentages of pendant groups, terminal carbon chains, and side chain groups are by mole, unless specified otherwise. Percent by mole is expressed as "mol %," and percent by weight is expressed as "wt %."

In the present disclosure, the length of a pendant group means the total number of carbon atoms in a carbon chain starting from the first carbon atom therein directly bonded to a carbon backbone of the molecule in question, and ending with the final carbon atom therein connected to no more than one carbon atom, without taking into consideration of any substituents on the chain. Preferably, the pendant group is free of substituents comprising more than 2 carbon atoms (or more than 1 carbon atom), or is free of any substituent.

In the present disclosure, all molecular weight data are in the unit of g·mol$^{-1}$. Molecular weight of oligomer or polymer materials (including hydrogenated and uPAO materials) and distribution thereof in the present disclosure are measured by using gel permeation chromatography (GPC) equipped with a multiple-channel band filter based infrared detector ensemble IR5 (GPC-IR) with band region covering from 2700-3000 cm$^{-1}$ (all saturated C—H stretching vibration). Reagent grade 1,2,4-trichlorobenzene (TCB) (from Sigma-Aldrich) comprising 300 ppm antioxidant BHT is used as the mobile phase at a nominal flow rate of 1.0 mL/min and a nominal injection volume 200 μL. The whole system including transfer lines, columns, and detectors is contained in an oven maintained at 145° C. A given amount of sample is weighed and sealed in a standard vial with 10 μL flow marker (heptane) added thereto. After loading the vial in the auto-sampler, the oligomer or polymer is automatically dissolved in the instrument with 8 mL added TCB solvent at 160° C. with continuous shaking. The sample solution concentration is from 0.2 to 2.0 mg/ml, with lower concentrations used for higher molecular weight samples. The concentration, c, at each point in the chromatogram is calculated from the baseline-subtracted IR5 broadband signal, I, using the equation: $c=\alpha I$, where $\alpha$ is the mass constant determined with polyethylene or polypropylene standards. The mass recovery is calculated from the ratio of the integrated area of the concentration chromatography over elution volume and the injection mass which is equal to the pre-determined concentration multiplied by injection loop volume. The molecular weight is determined by combining universal calibration relationship with Mark-Houwink equation in which the M-H parameters a/K=0.695/0.00012 for mPAO. Number-average molecular weight (Mn) and weight-average molecular weight (Mw) of an oligomer or polymer are obtained from the above process. The polydispersity index (PDI) of the material is then calculated as follows:

$$PDI=Mw/Mn.$$

NMR spectroscopy provides key structural information about the synthesized polymers. Proton NMR (1H-NMR) analysis of the unsaturated PAO product gives a quantitative breakdown of the olefinic structure types (viz. vinyl, 1,2-di-substituted, tri-substituted, and vinylidene). In the present disclosure, compositions of mixtures of olefins comprising terminal olefins (vinyls and vinylidenes) and internal olefins (1,2-di-substituted vinylenes and tri-substituted vinylenes) are determined by using $^1$H-NMR. Specifically, a NMR instrument of at least a 500 MHz is run under the following conditions: a 30° flip angle RF pulse, 120 scans, with a delay of 5 seconds between pulses; sample dissolved in CDCl$_3$ (deuterated chloroform); and signal collection temperature at 25° C. The following approach is taken in determining the concentrations of the various olefins among all of the olefins from an NMR spectrum. First, peaks corresponding to different types of hydrogen atoms in vinyls (T1), vinylidenes (T2), 1,2-di-substituted vinylenes (T3), and tri-substituted vinylenes (T4) are identified at the peak regions in TABLE I below. Second, areas of each of the above peaks (A1, A2, A3, and A4, respectively) are then integrated. Third, quantities of each type of olefins (Q1, Q2, Q3, and Q4, respectively) in moles are calculated (as A1/2, A2/2, A3/2, and A4, respectively). Fourth, the total quantity of all olefins (Qt) in moles is calculated as the sum total of all four types (Qt=Q1+Q2+Q3+Q4). Finally, the molar concentrations (C1, C2, C3, and C4, respectively, in mol %) of each type of olefin, on the basis of the total molar quantity of all of the olefins, is then calculated (in each case, Ci=100*Qi/Qt).

TABLE I

| Type No. | Olefin Structure | Peak Region (ppm) | Peak Area | Hydrogen Atoms | Number of Quantity of Olefin (mol) | Concentration of Olefin (mol %) |
|---|---|---|---|---|---|---|
| T1 | $CH_2=CH-R^1$ | 4.95-5.10 | A1 | 2 | Q1 = A1/2 | C1 |
| T2 | $CH_2=CR^1R^2$ | 4.70-4.84 | A2 | 2 | Q2 = A2/2 | C2 |
| T3 | $CHR^1=CHR^2$ | 5.31-5.55 | A3 | 2 | Q3 = A3/2 | C3 |
| T4 | $CR^1R^2=CH\,R^3$ | 5.11-5.30 | A4 | 1 | Q4 = A4 | C4 |

Carbon-13 NMR ($^{13}$C-NMR) is used to determine tacticity of the PAOs of the present disclosure. Carbon-13 NMR can be used to determine the percentages of the triads, denoted (m,m)-triads (i.e., meso, meso), (m,r)- (i.e., meso, racemic) and (r,r)- (i.e., racemic, racemic) triads, respectively. The concentrations of these triads defines whether the polymer is isotactic, atactic or syndiotactic. In the present disclosure, the percentage of the (m,m)-triads in mol % is recorded as the isotacticity of the PAO material. Spectra for a PAO sample are acquired in the following manner. Approximately 100-1000 mg of the PAO sample is dissolved in 2-3 ml of chloroform-d for $^{13}$C-NMR analysis. The samples are run with a 60 second delay and 90° pulse with at least 512 transients. The tacticity was calculated using the peak around 35 ppm ($CH_2$ peak next to the branch point). Analysis of the spectra is performed according to the paper by Kim, I.; Zhou, J.-M.; and Chung, H. Journal of Polymer Science: Part A: Polymer Chemistry 2000, 38 1687-1697. The calculation of tacticity is mm*100/(mm+mr+rr) for the molar percentages of (m,m)-triads, mr*100/(mm+mr+rr) for the molar percentages of (m,r)-triads, and rr*100/(mm+mr+rr) for the molar percentages of (r,r)-triads. The (m,m)-triads correspond to 35.5-34.55 ppm, the (m,r)-triads to 34.55-34.1 ppm, and the (r,r)-triads to 34.1-33.2 ppm.

I. the Unsaturated PAO Product

PAOs are oligomeric or polymeric molecules produced from the polymerization reactions of alpha-olefin monomer molecules in the presence of a catalyst system. An uPAO molecule in the material of the present disclosure contains a C=C bond therein. Each uPAO molecule has a carbon chain with the largest number of carbon atoms, which is designated the carbon backbone of the molecule. Any non-hydrogen group attached to the carbon backbone other than to the carbon atoms at the very ends thereof is defined as a pendant group. The number of carbon atoms in the longest carbon chain in each pendant group is defined as the length of the pendant group. The backbone typically comprises the carbon atoms derived from the C=C bonds in the monomer molecules participating in the polymerization reactions, and additional carbon atoms from monomer molecules and/or molecules in the catalyst system that form the two ends of the backbone. A typical uPAO molecule can be represented by the following formula (F-1):

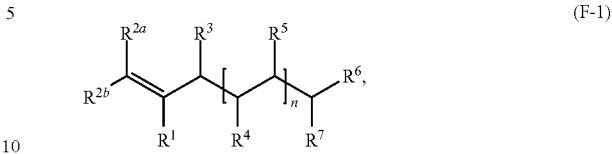

(F-1)

where $R^1$, $R^{2a}$, $R^{2b}$, $R^3$, each of $R^4$ and $R^5$, $R^6$, and $R^7$, the same or different at each occurrence, independently represents a hydrogen or a substituted or unsubstituted hydrocarbyl (preferably an alkyl) group, and n is a non-negative integer corresponding to the degree of polymerization. Where $R^1$, $R^{2a}$ and $R^{2b}$ are all hydrogen, (F-1) represents a vinyl; where $R^1$ is not hydrogen, and both $R^{2a}$ and $R^{2b}$ are hydrogen, (F-1) represents a vinylidene; and where $R^1$ is hydrogen, and only one of $R^{2a}$ and $R^{2b}$ is hydrogen, (F-1) represents a di-substituted vinylene; and where $R^1$ is not hydrogen, and only one of $R^{2a}$ and $R^{2b}$ is hydrogen, then (F-1) represents a tri-substituted vinylene.

Where n=0, (F-1) represents an uPAO dimer produced from the reaction of two monomer molecules after a single addition reaction between two C=C bonds.

Where n=m, m being a positive integer, (F-1) represents a molecule produced from the reactions of m+2 monomer molecules after m+1 steps of addition reactions between two C=C bonds.

Thus, where n=1, (F-1) represents a trimer produced from the reactions of three monomer molecules after two steps of addition reactions between two C=C bonds.

Assuming a carbon chain starting from $R^1$ and ending with $R^7$ has the largest number of carbon atoms among all straight carbon chains existing in (F-1), that carbon chain starting from $R^1$ and ending with $R^7$ having the largest number of carbon atoms constitutes the carbon backbone of the unsaturated PAO product molecule (F-1). $R^2$, $R^3$, each of $R^4$ and $R^5$, and $R^6$, which can be substituted or unsubstituted hydrocarbyl (preferably alkyl) groups, are pendant groups (if not hydrogen).

If only alpha-olefin monomers are used in the polymerization process, and no isomerization of the monomers and oligomers ever occurs in the reaction system during polymerization, about half of $R^1$, $R^2$, $R^3$, all $R^4$ and $R^5$, $R^6$, and $R^7$ would be hydrogen, and one of $R^1$, $R^2$, $R^6$, and $R^7$ would be a methyl, and about half of groups $R^1$, $R^2$, $R^3$, all $R^4$ and $R^5$, $R^6$, and $R^7$ would be hydrocarbyl groups introduced from the alpha-olefin monomer molecules. In a specific example of such case, assuming $R^{2a}$ and $R^{2b}$ are hydrogen, $R^3$, all $R^5$, and $R^6$ are hydrogen, and $R^1$, all $R^4$, and $R^7$ have 8 carbon atoms in the longest carbon chains contained therein, and n=8, then the carbon backbone of the (F-1) PAO molecule would comprise 35 carbon atoms, and the average pendant group length of the pendant groups ($R^2$, and all of $R^4$) would be 7.22 (i.e., (1+8*8)/9). This uPAO molecule, which can be produced by polymerizing 1-decene using certain metallocene catalyst systems described in greater detail below, can be represented by formula (F-2) below:

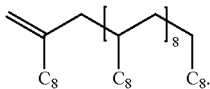

(F-2)

In this molecule, the longest 5%, 10%, 20%, 40%, 50%, and 100% of the pendant groups have average pendant group length of Lpg(5%) of 8, Lpg(10%) of 8, Lpg(20%) of 8, Lpg(50%) of 8, and Lpg(100%) of 7.22, respectively.

Depending on the polymerization catalyst system used, however, different degrees of isomerization of the monomers and/or oligomers can occur in the reaction system during the polymerization process, resulting in different degrees of substitution on the carbon backbone. In a specific example of such case, assuming $R^{2a}$ and $R^{2b}$ are both hydrogen, $R^3$ and all $R^5$ are methyl, $R^6$ is hydrogen, $R^1$ has 8 carbon atoms in the longest carbon chain contained therein, all $R^4$ and $R^7$ have 7 carbon atoms in the longest carbon chain contained therein, and n=8, then the carbon backbone of the (F-1) uPAO molecule would comprise 34 carbon atoms, and the average pendant group length of the pendant groups ($R^2$, all $R^4$, and $R^5$) would be 3.67 (i.e., (1+1+7*8+1*8)/18). This uPAO molecule, which may be produced by polymerizing 1-decene using certain non-metallocene catalyst systems described in greater detail below, can be represented by the following formula (F-3):

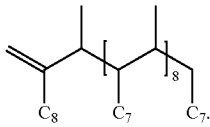

(F-3)

In this molecule, the longest 5%, 10%, 20%, 40%, 50%, and 100% of the pendant groups have average pendant group lengths of Lpg(5%) of 7, Lpg(10%) of 7, Lpg(20%) of 7, Lpg(50%) of 6.3, and Lpg(100%) of 3.67, respectively.

One skilled in the art, with knowledge of the molecular structure or the monomer used in the polymerization step for making the unsaturated PAO product, the process conditions (catalyst used, reaction conditions, e.g.), and the polymerization reaction mechanism, can determine the molecular structure of the uPAO molecules, hence the pendant groups attached to the carbon backbone, and hence the Lpg(5%), Lpg(10%), Lpg(20%), Lpg(50%), and Lpg(100%), respectively.

Alternatively, one skilled in the art can determine the Lpg(5%), Lpg(10%), Lpg(20%), Lpg(50%), and Lpg(100%) values of a given unsaturated PAO product by using separation and characterization techniques available to polymer chemists. For example, gas chromatography/mass spectroscopy machines equipped with boiling point column separator can be used to separate and identify individual chemical species and fractions; and standard characterization methods such as NMR, IR, and UV spectroscopy can be used to further confirm the structures.

The unsaturated PAO products of the present disclosure may be a homopolymer made from a single alpha-olefin monomer or a copolymer made from a combination of two or more alpha-olefin monomers.

The unsaturated PAO product of the present disclosure is produced by using a catalyst system comprising a specific type of metallocene compound described in detail below. The unsaturated PAO product can be substantially free of the alpha-olefin monomer(s), and contains vinylidenes and tri-substituted vinylenes at a high concentration, desirably in the range from c1 to c2 mol % in total, where c1 and c2 can be, independently, 50, 55, 60, 65, 70, 75, 80, 85, 90, 95, 98, based on the total moles of vinyls, vinylidenes, 1,2-di-substituted vinylenes, and tri-substituted vinylenes, as long as c1<c2. Preferably, c1=60, c2=90. More preferably, c1=70, c2=80. The high concentrations of vinylidenes and tri-substituted vinylenes are achieved partly by the unique structure of the metallocene compound used in the catalyst system. It is known that vinylidenes and tri-substituted vinylenes are more reactive than 1,2-di-substituted vinylenes when reacted with many functionalizing agents. Thus, the high concentration of vinylidenes and tri-substituted vinylenes in the unsaturated PAO product of the present disclosure is particularly advantageous if the unsaturated PAO product is used as intermediates for making functionalized olefins.

Between the vinylidenes and tri-substituted vinylenes in the unsaturated PAO product of the present disclosure, vinylidenes tend to have a higher concentration than the tri-substituted vinylenes. Desirably, in the unsaturated PAO product of the present disclosure, the concentration of vinylidenes can range from c3 to c4 mol %, based on the total moles of the vinyls, vinylidenes, 1,2-di-substituted vinylenes, and tri-substituted vinylenes, where c3 and c4 can be, independently, 45, 50, 55, 60, 65, 70, 75, 80, 85, 90, as long as c3<c4. Preferably c3=50, c4=75. More preferably c3=55, c4=70.

The unsaturated PAO product desirably contains 1,2-di-substituted vinylenes at a low concentration in the range from c5 to c6 mol %, based on the total moles of vinyls, vinylidenes, 1,2-di-substituted vinylenes, and tri-substituted vinylenes in the unsaturated PAO product, where c5 and c6 can be 0, 0.1, 0.2, 0.4, 0.5, 0.6, 0.8, 1, 2, 3, 4, 5, 6, 7, 8, 9, 10, 11, as long as c5<c6. Preferably c5=0.1, c6=8. More preferably c5=0.5, c6=5. Such low concentration of 1,2-di-substituted vinylenes in the unsaturated PAO product is achieved by the low selectivity toward these olefins in the polymerization reactions, which is enabled again by the unique structure of the metallocene compound in the catalyst system used in the polymerization reaction.

Depending on the metallocene compound used in the catalyst system, the unsaturated PAO product of the present disclosure can contain vinyls at a very low concentration, e.g., from c7 to c8 mol %, based on the total moles of vinyls, vinylidenes, 1,2-di-substituted vinylenes, and tri-substituted vinylenes in the unsaturated PAO product, where c7 and c8 can be 0, 0.5, 1, 2, 3, 4, 5, 6, 7, 8, 9, 10, as long as c7<c8. Preferably c7=0, c8=8. More preferably c7=0, c8=5. Such low concentration of vinyls in the unsaturated PAO product can be achieved by the low selectivity toward vinyls in the polymerization reactions, which can be enabled by choosing the molecular structure of the metallocene compound in the catalyst system used in the polymerization reaction as described below in connection with the description of the process for making the unsaturated PAO product.

Depending on the metallocene compound used in the catalyst system, the unsaturated PAO product of the present disclosure can contain vinyls at a relatively high concentration, e.g., from c9 to c10 mol %, based on the total moles of vinyls, vinylidenes, 1,2-di-substituted vinylenes, and tri-substituted vinylenes in the unsaturated PAO product, where c9 and c10 can be 12, 14, 15, 16, 18, 20, 22, 24, 25, 26, 28, 30, 32, 34, 35, 36, 38, 40, as long as c9<c10. Preferably c9=15, c10=30. More preferably c9=15, c10=25. Such high concentration of vinyls in the unsaturated PAO product can be achieved by a high selectivity toward vinyls in the polymerization reactions, which can be enabled by choosing the molecular structure of the metallocene compound in the catalyst system used in the polymerization reaction as described below in connection with the description of the process for making the unsaturated PAO product. Moreover, such high concentration of vinyls and low concentrations of 1,2-di-substituted vinylenes can be achieved simultaneously by carefully choosing the metallocene compound used in the catalyst system for the polymerization reaction.

Thus, the unsaturated PAO product of the present disclosure comprises a plurality of oligomeric and/or polymeric PAO molecules, which may be the same or different. Each uPAO molecule comprises a plurality of pendant groups, which may be the same or different, and the longest 5%, 10%, 20%, 40%, 50%, and 100% of the pendant groups of all of the olefin molecules of the unsaturated PAO product have an average pendent group length of Lpg(5%), Lpg(10%), Lpg(20%), Lpg(40%), Lpg(50%), and Lpg(100%), respectively. It is preferred that at least one of the following conditions are met:

(i) $a1 \leq Lpg(5\%) \leq a2$, where a1 and a2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0 15.5, 16.0, as long as a1<a2;

(ii) $b1 \leq Lpg(10\%) \leq b2$, where b1 and b2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as b1<b2;

(iii) $c1 \leq Lpg(20\%) \leq c2$, where c1 and c2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as c1<c2;

(iv) $d1 \leq Lpg(40\%) \leq d2$; where d1 and d2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, 14.5, 15.0, as long as d1<d2;

(v) $e1 \leq Lpg(50\%) \leq e2$; where e1 and e2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, 13.5, 14.0, as long as e1<e2; and (vi) $f1 \leq Lpg(100\%) \leq f2$, where f1 and f2 can be, independently, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.0, as long as f1<f2.

Preferably, at least 60% of the pendent groups on olefin molecules in the unsaturated PAO product are straight chain alkyls having at least 4 (or at least 6, or at least 8, or at least 10, or at least 12) carbon atoms. Preferably, at least 90% of the pendent groups on the olefin molecules in the unsaturated PAO product are straight chain alkyls having at least 4 (or at least 6, or at least 8, or at least 10, or at least 12) carbon atoms.

The unsaturated PAO product of the present disclosure may have various levels of regio-regularity. For example, each uPAO molecule may be substantially atactic, isotactic, or syndiotactic. A category of the metallocene compounds used in the processes of the present disclosure lack C1, C2, and Cs symmetry. Without intending to be bound by a particular theory, it is believed that PAO materials made by using such asymmetrical metallocene-based catalyst system tend to be atactic.

The unsaturated PAO product of the present disclosure can have viscosity varying in a broad range. For example, the unsaturated PAO product may have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt. The exact viscosity of the unsaturated PAO product can be controlled by, e.g., monomer used, polymerization temperature, polymerization reactor residence time, catalyst used, concentration of catalyst used, distillation and separation conditions, and mixing multiple unsaturated PAO products with different viscosity.

In addition, the unsaturated PAO product of the present disclosure advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8). A narrow molecular weight distribution of the uPAO molecules can be achieved by using metallocene-compound-based catalyst systems in the polymerization step under controlled polymerization conditions (temperature fluctuation, residence time, and the like). Such narrow PDI is desirable in that it defines a material with a high degree of homogeneity in molecular weight, molecular size, rheology behavior, viscosity index, and degrading behavior (such as shear stability and oxidation stability). From an olefin mixture with such degree of homogeneity one can produce a functionalized material having a similar degree of homogeneity as well.

In general, the olefin mixture in the unsaturated PAO product of the present disclosure can have an average molecular weight that varies widely (and correspondingly, a KV100 that varies widely). Typically, the olefin mixture has a number average molecular weight of Mw, where $Mw1 \leq Mw \leq Mw2$, where Mw1 and Mw2 can be, independently, 100, 200, 300, 400, 500, 600, 700, 800, 900, 1000, 2000, 3000, 4000, 5000, 6000, 7000, 8,000, 9000, 10,000, 20,000, 30,000, 40,000, or even 50,000, as long as Mw1<Mw2.

The unsaturated PAO product of the present disclosure may comprise, in addition to the olefin mixture, saturated hydrocarbons. The saturated hydrocarbons may be produced in-situ in the polymerization step of the alpha-olefin for making the unsaturated PAO product, e.g., where the polymerization is conducted in the presence of hydrogen ($H_2$) such as a hydrogen-containing atmosphere. Alternatively or additionally, the saturated hydrocarbons may be produced by a partial hydrogenation of a portion of the unsaturated PAO product as produced from the polymerization step. Still alternatively, the saturated hydrocarbon may be blended with an olefin mixture to obtain a mixture of desired property and composition. Nonetheless, it is desired that the unsaturated PAO product of the present disclosure comprises the vinylidene, tri-substituted vinylenes, optional vinyls and optional 1,2-di-substituted vinylenes at a total concentration thereof of at least 50 wt % (or at least 60, 65, 70, 75, 80, 85, 90, 92, 94, 95, 96, 97, 98, or 99 wt %) based on the total weight of the unsaturated PAO product.

In general, it is desired that the unsaturated PAO product of the present disclosure has a bromine number in a range from Nb(PAO)1 to Nb(PAO)2, where Nb(PAO)1 and Nb(PAO)2 can be, independently, 1.0, 1.5, 2.0, 2.5, 3.0, 3.5, 4.0, 4.5, 5.0, 6.0, 7.0, 8.0, 9.0, or even 10.0, 15.0, 10.0, as long as Nb(PAO)1<Nb(PAO)2. Desirably, a great majority, such as at least 80, 85, 90, 95, 98, or even 99 mol % of the molecules in the unsaturated PAO product of the present disclosure is unsaturated. Desirably, each unsaturated PAO molecule is capable of addition reaction with one $Br_2$ molecule to obtain a 1,2-dibromo-derivative thereof.

Molecular structures of exemplary vinylidene uPAOs made from a mixture of 1-octene and 1-dodecene alpha-olefin monomers at a molar ratio of 4:1 can be schematically represented by formula (F-V) as follows, where n can be any integer.

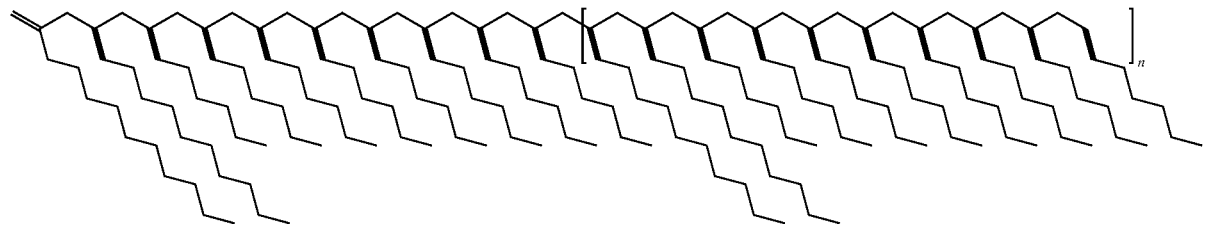

The two C10 pendant groups are shown to be next to each other. In real molecules, they may be randomly distributed among all of the pendant groups. The structure shows nearly 100% isotacticity, i.e., 100 mol % of (m,m)-triads in the structure. In real molecules, a small fraction may be (m,r)- or (r,r)-triads. Nonetheless, each of the long pendant groups can extend to form a substantially linear chain, and interact with other long straight carbon chains from other uPAO molecules and other molecules in its vicinity.

Because of the presence of the C=C bonds in the uPAO molecules, when exposed to $O_2$ molecules (such as when exposed to air), the unsaturated PAO product can be oxidized if not protected by a more reactive material toward $O_2$. To that end, in the unsaturated PAO product, anti-oxidant materials may be added to prolong its shelf life and facilitate handling, storage, and transportation thereof. Such anti-oxidants can include, but are not limited to, those anti-oxidants typically used in lubricant base stocks and lubricating oil compositions. Non-limiting examples of such anti-oxidants and the use quantity thereof are given in paragraphs [0101]-[0108], pages 9 and 10 of U.S. Patent Application Publication No. 2010/0087349 A1, the content of which is incorporated by reference in its entirety.

II. Use of the Unsaturated PAO Product of the Present Disclosure

The unsaturated PAO product of the present disclosure as described above, desirably produced by polymerization of alpha-olefin monomers in the presence of a metallocene-compound-based catalyst system, can be advantageously used as a chemical intermediate for making many products, especially those comprising a PAO molecule moiety and one or more functional groups. The hydrocarbon molecules in the unsaturated PAO product, if prepared from the polymerization of alpha-olefin monomers containing only one C=C double bond in their molecules, tend to comprise no more than one C=C bond each, with the rest of its structure consisting of C—C bonds and C—H bonds.

For example, one can subject the unsaturated PAO product of the present disclosure to a step of hydrogenation by contacting it with a hydrogen-containing atmosphere in the presence of a hydrogenation catalyst, such as one containing one or more of Fe, Co, Ni, precious metals (such as Ru, Rh, Pd, Os, Ir, Pt), and the like. Because of the composition of the unsaturated PAO product of the present disclosure, they can be advantageously hydrogenated to convert a great majority of the C=C bonds present in the olefin molecules into carbon-carbon single bonds, thereby achieving a material that is substantially aliphatic and saturated characterized by a low Bromine number of no greater than 5.0, preferably no greater than 4.0, more preferably no greater than 3.0, most preferably no greater than 2.0. Such hydrogenated, largely aliphatic hydrocarbon materials have high viscosity index, low pour point, high oxidation stability and high shear stability. They are advantageously used as, e.g., base stocks for lubricant compositions, such as those used in internal combustion engines, automotive grease oils, industrial grease oils, gear box oils, and the like.

As mentioned above, the C=C bonds present in the molecules of the unsaturated PAO product of the present disclosure are highly reactive, and therefore can react with multiple, different types of chemical agents having useful functional groups, thereby creating a PAO molecule further comprising a functional group bonded thereto. The functional group can comprise, in turn, other functional groups, which can react with additional chemical agents, bringing additional or different functional groups to the final molecule. The hydrocarbon substrate (i.e., the PAO structure) of thus functionalized PAO can impart desired properties to the functionalized material, such as solubility in organic media or hydrophobicity, and the functional groups can impart other desired properties to the final material, such as polarity, hydrophilicity (thus, solubility in aqueous media), and the like, making the final material particularly useful where such dual properties are desired (e.g., detergents).

U.S. Publication No. 2014/0087986 A1 discloses multiple methods for making functionalized PAO from unsaturated PAO products produced by polymerization of alpha-olefin monomers in the presence of a metallocene-compound-based catalyst system. The entirety of the disclosure of this reference is incorporated by reference.

It is highly desired that upon functionalization of the unsaturated PAO product, the C=C double bond in the reacted uPAO molecule becomes saturated (i.e., each carbon atom in the original C=C bond is then bonded to four atoms). This can be achieved by using functionalization agents reactive substantially only toward the C=C bonds, but substantially inert toward the C—C bonds and C—H bonds in the uPAO olefin molecules under the functionalization conditions. Given that each uPAO olefin molecule comprises typically only one C=C bond, the uPAO olefin molecule would then become saturated upon such functionalization reaction.

Upon functionalization of the C=C bond in the uPAO olefin molecule, the overall structure of the functionalized PAO molecule would be substantially similar to that of a hydrogenated PAO molecule where the C=C bond has been saturated by hydrogenation as described above. Assuming that the bond between the functional group(s) to the carbon atom(s) is not significantly less robust than the C—C and C—H bonds, and assuming the functional group(s) per se are not significantly less robust than a pendant group on the PAO molecule under the use conditions, one can expect a stable oligomeric/polymeric structure retaining at least some of the interesting and useful properties of a saturated PAO molecule, such as one or more of viscosity index, oxidation stability, shear stability, Bromine number, and the like. The retained properties can make the functionalized PAO material particularly useful in applications typical for the saturated PAO materials, such as lubricating oil compositions, and the like.

It is highly desirable that the functionalization agent used to functionalize the unsaturated PAO product is highly selective toward reacting with the C=C bond only, and is substantially inert with respect to the C—C bonds and C—H bonds on the uPAO molecules.

This can ensure the production of functionalized PAO molecules each comprising one or two functional group(s) only, and a complete functionalization of substantially all of the uPAO molecules if desired. In applications such as lubricating oil compositions, because of the high reactivity of C=C bonds in the uPAO molecules, it may be desired that substantially all of the C=C bonds in the uPAO molecules are saturated before the functionalized PAO material is put into the oil compositions, either as a base stock or as an additive.

Additionally and alternatively, one may also functionalize the uPAO molecules by substituting one or more of the hydrogen atoms on the carbon backbone or one of the pendant groups with a functional group by using chemical agents known to be reactive with C—H bonds. Because a uPAO molecule typically comprise many C—H bonds at multiple locations, such reaction would be less selective than selective functionalization of C=C bonds by using a functionalization agent that is inert to the C—H bonds, and can result in very large number of very different molecules, and thus is less desirable than functionalization selective toward the C=C bonds only.

III. Hydrogenated PAO Product

The unsaturated PAO product made by the method of the present disclosure can be directly used as a lubricating oil base stock and other applications because it can be made to have the desired physical properties, particularly rheological properties interesting for such applications. However, due to the presence of a C=C bonds on a large portion, if not all, of the uPAO molecules, direct use thereof as a lubricating oil base stock can cause stability issues to the oil if the oil is exposed to an oxidative environment, such as the air. Thus, in general, for lubricating oil applications, it is highly desirable that the unsaturated PAO product is hydrogenated to remove at least a portion, preferably a major portion of the C=C bonds in the PAO molecules. Hydrogenation can be performed by contacting the unsaturated PAO product of the present disclosure with a hydrogen-containing atmosphere in the presence of a hydrogenation catalyst, such as a transition-metal-based catalyst. Metals such as Fe, Co, Ni, precious metals (Ru, Rh, Pd, Re, Os, Ir, Pt) are known to be catalytically active for hydrogenating olefins and therefore can be used for catalyzing the hydrogenation of the unsaturated PAO product of the present disclosure to make a substantially hydrogenated, aliphatic, and saturated PAO material. Such hydrogenated PAO material can be characterized by a low bromine number of no greater than 5.0, preferably no greater than 4.0, more preferably no greater than 3.0, most preferably no greater than 2.0. Such hydrogenated, largely aliphatic hydrocarbon materials have high viscosity index, low pour point, high oxidation stability and high shear stability.

The hydrogenated PAO product made from hydrogenating the unsaturated PAO product will have viscosity, molecular weight distribution, pendent group distribution, polydispersity index, that are almost identical with those of the precursor unsaturated PAO product.

Thus, the hydrogenated PAO product of the present disclosure can have a KV100 in a range from 1 to 5000 cSt, such as 1 to 3000 cSt, 2 to 2000 cSt, 2 to 1000 cSt, 2 to 800 cSt, 2 to 600 cSt, 2 to 500 cSt, 2 to 400 cSt, 2 to 300 cSt, 2 to 200 cSt, or 5 to 100 cSt.

The hydrogenated PAO product of the present disclosure advantageously have a low polydispersity index (PDI) in the range from about 1.0 to about 5.0 (e.g., from 1.2 to 4.0, from 1.3 to 3.0, from 1.4 to 2.5, from 1.5 to 2.0, or from 1.6 to 1.8. Such narrow PDI is desirable in that it defines a material with a high degree of homogeneity in molecular weight, molecular size, rheology behavior, viscosity index, and degrading behavior (such as shear stability and oxidation stability).

The hydrogenated PAO product of the present disclosure can have a number average molecular weight of Mw, where $Mw1 \leq Mw \leq Mw2$, and Mw1 and Mw2 can be, independently, 100, 200, 300, 400, 500, 600, 700, 800, 900, 1000, 2000, 3000, 4000, 5000, 6000, 7000, 8,000, 9000, 10,000, 20,000, 30,000, 40,000, or even 50,000, as long as $Mw1 < Mw2$.

The hydrogenated PAO can be used as a high-quality API Group IV base stock. Various grades of the hydrogenated mPAO with KV100 varying from very low such as 1 cSt to very high such as 5,000 cSt can be made by using the method of the present disclosure, and used for blending with each other and other API Group I, II, III, IV, or V base stocks to make high-quality lubricating oil formulations, such as internal combustion engine oils, automobile drive line oils, industrial oils, greases, and the like. Furthermore, the mPAO can be used as heat transfer oil (e.g., transformer oil), processing oil, hydraulic power transfer oil, and the like.

IV. The Catalyst System

IV.1 The Metallocene Compound

The metallocene compound used in the process of the present disclosure for making PAOs generally has a structure represented by formula (F-MC) below comprising a first Cp ring directly connected with $R^1$, $R^2$, $R^3$, and $R^4$ and a second Cp ring directly connected with $R^5$, $R^6$, $R^7$, and $R^8$:

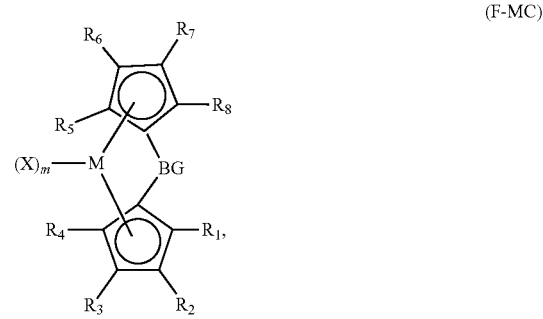

(F-MC)

wherein:

$R^1$ and $R^4$ are each independently a hydrogen, a substituted or unsubstituted linear, branched linear, or cyclic C1-C30 (preferably C1-C20, more preferably C1-C10)

hydrocarbyl group (preferably alkyl, cycloalkyl, alkenyl, cycloalkenyl, aryl, more preferably alkyl and alkenyl, still more preferably alkyl), $R^2$ and $R^3$ are each independently a substituted or unsubstituted linear, branched linear, or cyclic C1-C50 (preferably C1-C40, more preferably C1-C30, more preferably C1-C20, still more preferably C1-C10) hydrocarbyl group (preferably alkyl, cycloalkyl, alkenyl, cycloalkenyl, aryl, more preferably alkyl and alkenyl, still more preferably alkyl), or alternatively, two or more of $R^1$, $R^2$, $R^3$, and $R^4$, taken together, with the carbon atoms in the first Cp ring to which they are directly connected, form one or more substituted or unsubstituted ring annelated to the first Cp ring;

$R^5$, $R^6$, $R^7$, and $R^8$ are each independently hydrogen, or a substituted or unsubstituted linear, branched linear, or cyclic C1-C30 (preferably C1-C20, more preferably C1-C10) hydrocarbyl group (preferably alkyl, cycloalkyl, alkenyl, cycloalkenyl, aryl, more preferably alkyl and alkenyl, still more preferably alkyl), provided: $R^6$ and $R^7$ are not both hydrogen; or alternatively, two or more of $R^5$, $R^6$, $R^7$, and $R^8$, taken together, with the intermediate carbon atoms in the second Cp ring to which they are directly connected, form one or more substituted or unsubstituted ring annelated to the second Cp ring;

provided, however, the first Cp ring and the second Cp ring are not annelated to ring structures simultaneously;

BG is a bridging group connected directly with both the first Cp ring and the second Cp ring;

M is a transition metal;

X, the same or different at each occurrence, is independently selected from halogens, C1-C50 substituted or unsubstituted linear, branched, or cyclic hydrocarbyl groups; and m is an integer equal to v-2, where v is the valency of M.

Preferably M is Ti, Zr or Hf. More preferably m is Zr or Hf.

Preferably both $R^1$ and $R^4$ are not hydrogen. Thus, $R^1$ and $R^4$ can be each independently a substituted or unsubstituted linear, branched linear, or cyclic C1-C30 (preferably C1-C10, more preferably C1-C8, more preferably C1-C6, still more preferably C1-C4, hydrocarbyl group). Preferred examples of $R^1$ and $R^4$ are: methyl, ethyl, n-propyl, isopropyl, n-butyl, 1-methylpropyl, 1-ethylethyl, n-pentyl, 1-methylpentyl, 1-ethylpropyl, 1-hexyl, 1-methylpentyl, 1-ethylbutyl, 1-propylpropyl, optionally substituted cyclohexyl, optionally substituted phenyl, optionally substituted benzyl, and the like, and any ethylenically unsaturated group that can be derived from them by eliminating one available hydrogen group from each of two adjacent carbon atoms therein. Alternatively, $R^1$ and $R^2$ may join together with the carbon atoms in the first Cp ring to which they are directly connected to form a substituted or unsubstituted ring structure annelated to the first Cp ring. Alternatively $R^3$ and $R^4$ may join together with the carbon atoms in the first Cp ring to which they are directly connected to form a substituted or unsubstituted ring structure annelated to the first Cp ring. Alternatively $R^2$ and $R^3$ may join together with the carbon atoms in the first Cp ring to which they are directly connected to form a substituted or unsubstituted ring structure annelated to the first Cp ring. Such ring annelated to the first Cp ring can be, e.g., a phenyl ring, a cyclohexyl ring, a naphthyl ring, a tetrahydronaphthyl ring, or a benzofuran ring. When both $R^1$ and $R^2$ join to form a ring and $R^3$ and $R^4$ join to form another ring annelated to the first Cp ring, the two rings annelated to the first Cp ring can be identical or different, such as one of any of the above enumerated rings.

The multi-ring system including the first Cp ring can be, e.g., an indenyl ring, a 9H-fluorenyl ring, a tetrahydroindenyl ring, and the like.

In one embodiment, at least one of $R^5$ and $R^8$ is hydrogen. Without intending to be bound by a particular theory, it is believed that where either one or both of $R^5$ and $R^8$ is hydrogen, the free space available on either or both side(s) of the bridging group -BG- favors the formation of vinylidene and vinylene chain ends, resulting in a relatively low selectivity toward vinyl chain ends in the polymerization reaction. The 1,2-di-substituted vinylene selectivity remains low, though. Thus, where a low vinyl selectivity and a low 1,2-di-substituted vinylene selectivity in the polymerization reaction is desired, at least one or $R^5$ and $R^8$ is preferred to be hydrogen. In certain embodiments, both $R^5$ and $R^8$ can be hydrogen.

Where both $R^5$ and $R^8$ are not hydrogen, steric hindrance caused by substituents next to the bridging group -BG- tends to result in higher selectivity toward vinyl chain ends in the polymerization reaction than those cases where at least one of $R^5$ and $R^8$ is hydrogen. The 1,2-di-substituted vinylene selectivity remains low, though. One can therefore choose such metallocene compounds for the catalyst system of the present disclosure if a high vinyl selectivity is desired at the expense of vinylidenes and vinylenes.

Both the first and second Cp rings in the metallocene compound of the present disclosure are substituted. One, but not both, of the first and second Cp rings can be annelated to one or more rings. Preferably, the molecule of the metallocene compound does not exhibit a C1, C2, or Cs symmetry. Without intending to be bound by any particular theory, it is believed that the unique structure as a result of the substitution/annelation of the two Cp rings favors the formation of certain chain ends in the polymerization reactions catalyzed by the metallocene compound, hence the higher selectivity toward those olefins. Particularly, the processes of the present invention using the catalyst system comprising these metallocene compounds generally have a high selectivity toward vinylidene and tri-substituted vinylenes, and a low selectivity toward vinylenes. In addition, in cases where metallocene compounds lacking a C1, C2, or Cs symmetry are used, the processes may produce atactic PAO materials.

The bridging group -BG- is preferably selected from:

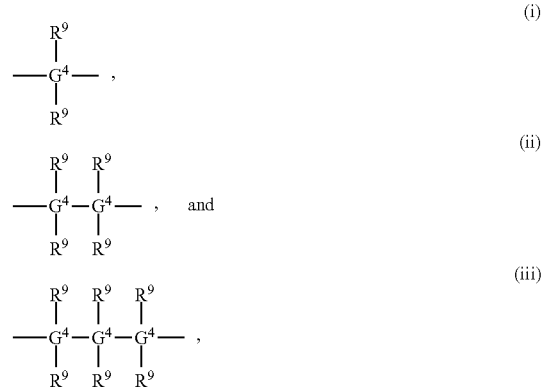

where groups G4 are, the same or different at each occurrence, independently selected from carbon, silicon, and germanium, and each $R^9$ is independently a C1-C30 substituted or unsubstituted linear, branched, or cyclic hydrocarbyl groups. Preferred $R^9$ includes substituted or unsubstituted methyl, ethyl, n-propyl, phenyl, and benzyl. Preferably -BG- is category (i) or (ii) above. More preferably -BG- is category (i) above. Preferably all $R^9$'s are identical.

Preferably each of the leaving group X is independently selected from substituted or unsubstituted methyl, ethyl, benzyl group, and halogen. Where M is Ti, Zr, or Hf, m is 2.

Particularly desirable metallocene compounds useful for the process of the present disclosure include the following compounds and their optical isomers (not shown):

I-1
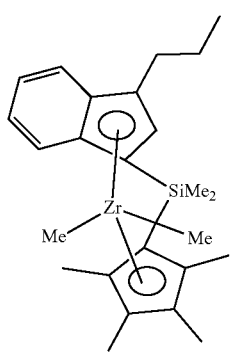

I-2

I-3

I-4
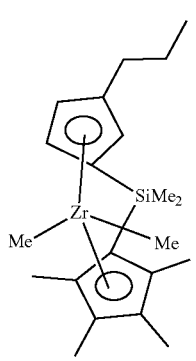

I-5
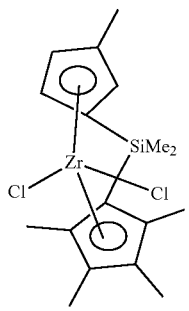

I-6
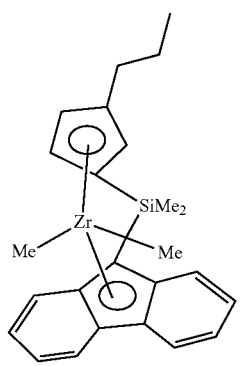

I-7
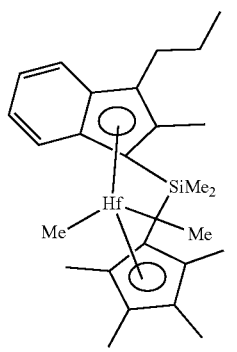

I-8
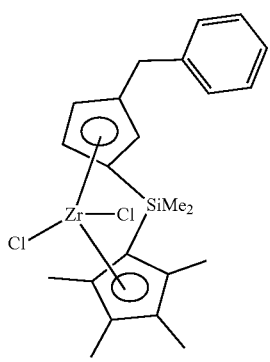

I-9

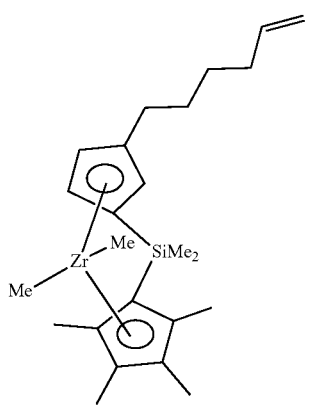

I-10

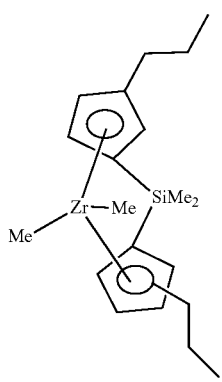

I-11

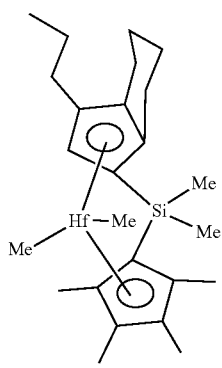

I-12

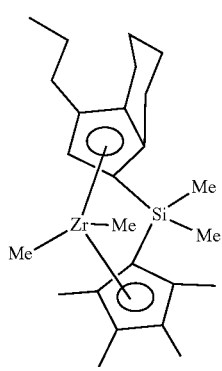

I-13

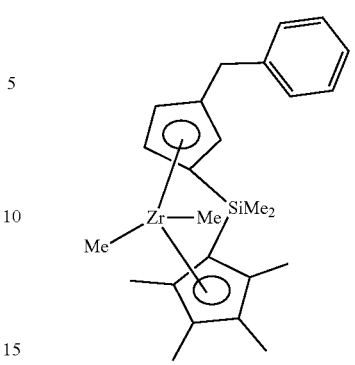

Metallocene compounds generally can be synthesized by using typical chemical reagents (e.g., halides of hafnium, zirconium, titanium) and intermediates (such as ligands containing one or two substituted or unsubstituted Cp ring, substituted or unsubstituted annelated Cp ring such as indenyl ring and tetrahydroindenyl ring, and the like) that are commercially available, and following the typical reactions exemplified in the synthesis examples in Part A of the Examples section of the present disclosure.

IV.2 Activators and Activation of the Metallocene Compound

The metallocene compounds, when activated by a commonly known activator such as non-coordinating anion activator, form active catalysts for the polymerization or oligomerization of olefins. Activators that may be used include Lewis acid activators such as triphenylboron, tris-perfluorophenylboron, tris-perfluorophenylaluminum and the like and or ionic activators such as dimethylanilinium tetrakisperfluorophenylborate, triphenylcarboniumtetrakis perfluorophenylborate, dimethylaniliniumtetrakisperfluorophenylaluminate, and the like.

A co-activator is a compound capable of alkylating the transition metal complex, such that when used in combination with an activator, an active catalyst is formed. Co-activators include alumoxanes such as methylalumoxane, modified alumoxanes such as modified methylalumoxane, and aluminum alkyls such trimethylaluminum, triisobutylaluminum, triethylaluminum, and tri-isopropylaluminum, tri-n-hexylaluminum, tri-n-octylaluminum, tri-n-decylaluminum or tri-n-dodecylaluminum. Co-activators are typically used in combination with Lewis acid activators and ionic activators when the pre-catalyst is not a dihydrocarbyl or dihydride complex. Sometimes co-activators are also used as scavengers to deactivate impurities in feed or reactors.

U.S. Pat. No. 9,409,834 B2 (line 39, column 21 to line 44, column 26) provides a detailed description of the activators and coactivators that may be used with the metallocene compound in the catalyst system of the present disclosure. The relevant portions of this patent are incorporated herein by reference in their entirety.

Additional information of activators and co-activators that may be used with the metallocene compounds in the catalyst system of the present disclosure can be found in U.S. Patent Application Publication No. 2013/0023633 A1 (paragraph [0178] page 16 to paragraph [0214], page 22). The relevant portions of this reference is incorporated herein by reference in their entirety.

IV.3 Scavenger

A scavenger is a compound that is typically added to facilitate oligomerization or polymerization by scavenging impurities. Some scavengers may also act as activators and may be referred to as co-activators. A co-activator which is not a scavenger may also be used in conjunction with an activator in order to form an active catalyst with a transition metal compound. In some embodiments, a co-activator can be pre-mixed with the transition metal compound to form an alkylated transition metal compound, also referred to as an alkylated catalyst compound or alkylated metallocene. To the extent scavengers facilitate the metallocene compound in performing the intended catalytic function, scavengers, if used, are sometimes considered as a part of the catalyst system.

U.S. Pat. No. 9,409,834 B2, line 37, column 33 to line 61, column 34 provides detailed description of scavengers useful in the process of the present invention for making PAO. The relevant portions in this patent on scavengers, their identities, quantity, and manner of use are incorporated herein in their entirety.

V. The Process for Making PAO

The process for making PAO of the present disclosure broadly includes a step of contacting a C4-C30 alpha-olefin feed with a catalyst system comprising a metallocene compound described above in a polymerization reactor under polymerization conditions to effect a polymerization reaction to obtain a polymerization reaction mixture comprising vinylidenes, tri-substituted vinylenes, optionally 1,2-di-substituted vinylenes, and optionally vinyls; and obtaining an unsaturated PAO product from the polymerization reaction mixture, wherein the unsaturated PAO product comprises vinylidenes, tri-substituted vinylenes, optionally 1,2-di-substituted vinylenes, and optionally vinyls.

V.1 The Monomer(s)

The alpha-olefin feed for making the PAO materials of the present disclosure may comprise one or more of C2-C32 alpha-olefins. Thus, the feed may comprise ethylene, propylene, C4 alpha-olefins, and C5 alpha-olefins. Preferably each of ethylene, propylene, C4 alpha-olefins (1-butene and 2-methyl-1-propene), and C5 alpha-olefins (1-pentene and various isomers of methyl-1-butene) is supplied to the polymerization reactor, each independently at no higher than c1 mol %, based on the total moles of the alpha-olefins supplied to the polymerization reactor, where c1 can be 50, 40, 30, 20, 10, 5, 4, 3, 2, 1, 0.5, 0.1, 0.01, for each of them. Preferably the alpha-olefin feed is substantially free of ethylene, propylene, C4 alpha-olefins, and C5 alpha-olefins.

Preferably the feed comprises (i) C2 and C3 alpha-olefins combined, or (ii) C2, C3, and C4 alpha-olefins combined, or (iii) C2, C3, C4, and C5 alpha-olefins combined, at a quantity of no higher than c2 mol %, based on the total moles of the alpha-olefins supplied to the polymerization reactor, where c2 can be 50, 40, 30, 20, 10, 5, 4, 3, 2, 1, 0.5, 0.1, 0.01. Preferably the alpha-olefin feed is substantially free of (i) C2 and C3 alpha-olefins combined, or (ii) C2, C3, and C4 alpha-olefins combined, or (iii) C2, C3, C4, and C5 alpha-olefins combined.

The feed may preferably comprise one or more of C4-C32 (preferably C6-C24, more preferably C6-C18, still more preferably C8-C18) alpha-olefins. Preferably substantially all alpha-olefins in the feed are C4-C32 (more preferably C6-C24, more preferably C6-C18, still more preferably C8-C18) alpha-olefins. "Substantially all" means at least 90 mol % (or at least: 92 mol %, 94 mol %, 95 mol %, 96 mol %, 98 mol %, 99%, or even 99.5 mol %), based on the total moles of the alpha-olefins present in the feed.

Preferably at least a portion (e.g., at least: 80 mol %, 85 mol %, 90 mol %, 95 mol %, 96 mol %, 98 mol %, even 99 mol %, or even 99.5 mol %) of the alpha-olefins present in the feed are linear alpha-olefins (LAOs), i.e., those without a branch attached to the carbon backbone thereof. Examples of preferred LAOs are 1-butene, 1-pentene, 1-hexene, 1-heptene, 1-octene, 1-nonene, 1-decene, 1-dodecene, 1-tetradecene, 1-hexadecene, 1-octadecene, 1-icocene, C22, C24, C26, C28, C30, and C32 LAOs. PAO products made from such LAOs by using the process of the present disclosure tend to have fewer branches and pendant groups, leading to more uniform PAO molecular structures, hence better performance for applications such as lubricant base stocks, lubricant additives, and the like.

Where a single alpha-olefin is fed to the polymerization reactor, the thus obtained PAO is a homopolymer. Homopolymers can have substantially uniform molecular structure, and accordingly desirable physical and rheological properties such as viscosity index. A homopolymer tends to have pendant groups attached to the carbon backbone with highly uniform length.

In certain situations, a mixture of two, three, or even more alpha-olefins in the feed is desired to produce a copolymer PAO product. To that end, alpha-olefins with the following combinations are particularly advantageous: C6/C8, C6/C10, C6/C12, C6/C14, C6/C16, C8/C10, C8/C12, C8/C14, C8/C16, C10/C12, C10/C14, C10/C16, C10/C18, C12/C14, C12/C16, C12/C18, C12/C20, C6/C8/C10, C6/C8/C12, C6/C8/C14, C6/C10/C12, C6/C10/C14, C8/C10/C12, C8/C10/C14, C8/C12/C14, C10/C12/C16, C10/C12/C18, C10/C14/C16, C10/C14/C18, and the like. Desirably, at least one of the alpha-olefins in the mixture feed is an LAO. More desirably, substantially all of the alpha-olefins in the mixture feed are LAOs.

Preferred alpha-olefin monomers are mono-olefins containing one C=C bond per monomer molecule, though those olefins containing two or more C=C bonds per monomer molecule can be used as well.

The alpha-olefins used herein can be produced directly from ethylene growth process as practiced by several commercial production processes, or they can be produced from Fischer-Tropsch hydrocarbon synthesis from $CO/H_2$ syngas, or from metathesis of internal olefins with ethylene, or from cracking of petroleum or Fischer-Tropsch synthetic wax at high temperature, or any other alpha-olefin synthesis routes. A preferred feed for this invention is preferably at least 80 wt % alpha-olefin (preferably linear alpha olefin), preferably at least 90 wt % alpha-olefin (preferably linear alpha olefin), more preferably 100% alpha-olefin (preferably linear alpha olefin). However, alpha-olefin mixtures can also be used as feeds in this invention, especially if the other components are internal-olefins, branched olefins, paraffins, cyclic paraffins, aromatics (such as toluene and or xylenes). These components have diluent effects and are believed to not have a substantial detrimental effect on the polymerization of alpha-olefins. In other words, the process described herein can selectively convert alpha-olefins in a mixture and leave the other components unreacted. This is particularly useful when ethylene is not present in the mixture. This technology can be used to separate out alpha-olefins from a mixture by selectively reacting them with polymerization or oligomerization catalyst systems completely eliminating the need to separate alpha-olefins from the remainder of the components in a mixed feed stream. This is economically advantageous, for example, in a process utilizing Fisher-Tropsch synthesis olefin product streams containing alpha-olefins, internal-olefins and branched olefins. Such a mixture can be fed to the oligomerization technology as described herein and to selectively react away the alpha-olefin. No separate step to isolate the alpha-olefin is needed. Another example of the utility of this process involves alpha-olefins produced by the metathesis of internal olefins with ethylene, which may contain some internal olefins. This mixed olefin base stock feed can be reacted as is in the polymerization/oligomerization process of the present invention, which selectively converts the alpha-olefins into lube products. Thus one can use the alpha-olefin for the base stock synthesis without having to separate the alpha-olefin from internal olefin. This can bring a significant improvement in process economics. The feed olefins can be the mixture of olefins produced from other linear alpha-olefin process containing C4 to C20 alpha-olefins as described in Chapter 3 "Routes to Alpha-Olefins" of the book Alpha Olefins Applications Handbook, Edited by G. R. Lappin and J. D. Sauer, published by Marcel Dekker, Inc. N.Y. 1989.

V.2 Feed Purification

Olefin feed and or solvents may be treated to remove catalyst poisons, such as peroxides, oxygen or nitrogen-containing organic compounds or acetylenic compounds before being supplied to the polymerization reactor. The treatment of the linear alpha-olefin with an activated 13 Angstrom molecular sieve and a de-oxygenate catalyst, i.e., a reduced copper catalyst, can increase catalyst productivity (expressed in terms of quantity of PAO produced per micromole of the metallocene compound used) more than 10-fold. Alternatively, the feed olefins and or solvents are treated with an activated molecular sieve, such as 3 Angstrom, 4 Angstrom, 8 Angstrom or 13 Angstrom molecular sieve, and/or in combination with an activated alumina or an activated de-oxygenated catalyst. Such treatment can desirably increase catalyst productivity 2- to 10-fold or more.

V.3 Polymerization Reaction

Many polymerization/oligomerization processes and reactor types used for metallocene-catalyzed polymerization or oligomerization such as solution, slurry, and bulk polymerization or oligomerization processed can be used in this invention. If a solid or supported catalyst is used, a slurry or continuous fixed bed or plug flow process is suitable. Preferably, the monomers are contacted with the metallocene compound and the activator in the solution phase, bulk phase, or slurry phase, preferably in a continuous stirred tank reactor or a continuous tubular reactor. Preferably, the temperature in any reactor used herein is from −10° C. to 250° C., preferably from 30° C. to 220° C., preferably from 50° C. to 180° C., preferably from 60° C. to 170° C. Preferably, the pressure in any reactor used herein is from 0.1 to 100 atmospheres, preferably from 0.5 to 75 atmospheres, preferably from 1 to 50 atmospheres. Alternatively, the pressure is any reactor used herein is from 1 to 50,000 atmospheres, preferably 1 to 25,000 atmospheres. Alternatively, the monomer(s), metallocene and activator are contacted for a residence time of 1 second to 100 hours, preferably 30 seconds to 50 hours, preferably 2 minutes to 6 hours, preferably 1 minute to 4 hours. Alternatively solvent or diluent is present in the reactor and is preferably selected from the group consisting of butanes, pentanes, hexanes, heptanes, octanes, nonanes, decanes, undecanes, dodecanes, tridecanes, tetradecanes, pentadecanes, hexadecanes, toluene, o-xylene, m-xylene, p-xylene, mixed xylenes, ethylbenzene, isopropylbenzene, and n-butylbenzene; preferably toluene and or xylenes and or ethylbenzene, normal paraffins (such as Norpar solvents available for ExxonMobil Chemical Company in Houston, Tex.), or isoparaffin solvents (such as Isopar® solvents available for ExxonMobil Chemical Company in Houston, Tex.). These solvents or diluents are usually pre-treated in same manners as the feed olefins.

Typically, in the processes of this invention, one or more metallocene compounds, one or more activators, and one or more monomers are contacted to produce polymer or oligomer. These catalysts may be supported and as such will be particularly useful in the known slurry, solution, or bulk operating modes conducted in single, series, or parallel reactors. If the catalyst, activator or co-activator is a soluble compound, the reaction can be carried out in a solution mode. Even if one of the components is not completely soluble in the reaction medium or in the feed solution, either at the beginning of the reaction or during or at the later stages of the reaction, a solution or slurry type operation is still applicable. In any instance, the catalyst system components, dissolved or suspended insolvents, such as toluene or other conveniently available aromatic solvents, or in aliphatic solvent, or in the feed alpha-olefin stream, are fed into the reactor under inert atmosphere (usually nitrogen or argon blanketed atmosphere) to allow the polymerization or oligomerization to take place. The polymerization or oligomerization can be run in a batch mode, where all the components are added into a reactor and allowed to react to a pre-designed degree of conversion, either to partial conversion or full conversion. Subsequently, the catalyst is deactivated by any possible means, such as exposure to air or water, or by addition of alcohols or solvents containing deactivating agents. The polymerization or oligomerization can also be carried out in a semi-continuous operation, where feeds and catalyst system components are continuously and simultaneously added to the reactor so as to maintain a constant ratio of catalyst system components to feed olefin(s). When all feeds and catalyst system components are added, the reaction is allowed to proceed to a pre-determined stage. The reaction is then discontinued by catalyst deactivation in the same manner as described for batch operation. The polymerization or oligomerization can also be carried out in a continuous operation, where feeds and catalyst system components are continuously and simultaneously added to the reactor so to maintain a constant ratio of catalyst system and feed olefins. The reaction product is continuously withdrawn from the reactor, as in a typical continuous stirred tank reactor (CSTR) operation. The residence times of the reactants are controlled by a pre-determined degree of conversion. The withdrawn product is then typically quenched in the separate reactor in a similar manner as other operation. Preferably, any of the processes to prepare PAO's described herein are continuous processes. Preferably the continuous process comprises the steps of a) continuously introducing a feed stream comprising at least 10 mol % of the one or more C5 to C24 alpha-olefins into a reactor, b) continuously introducing the metallocene compound and the activator into the reactor, and c) continuously withdrawing the polyalphaolefin from the reactor. Alternatively, the continuous process comprises the step of maintaining a partial pressure of hydrogen in the reactor of 200 psi (1379 kPa) or less, based upon the total pressure of the reactor, preferably 150 psi (1034 kPa) or less, preferably 100 psi (690 kPa) or less, preferably 50 psi (345 kPa) or less, preferably 25 psi (173 kPa) or less, preferably 10 psi (69 kPa) or less. Alternately the hydrogen, if present is present in the reactor at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less. Alternately the hydrogen, if present, is present in the feed at 1000 ppm or less by weight, preferably 750 ppm or less, preferably 500 ppm or less, preferably 250 ppm or less, preferably 100 ppm or less, preferably 50 ppm or less, preferably 25 ppm or less, preferably 10 ppm or less, preferably 5 ppm or less.

Preferred reactors range in size from 2 ml and up. Usually, it is preferable to use reactors larger than one liter in volume for commercial production. The production facility may have one single reactor or several reactors arranged in series or in parallel or in both to maximize productivity, product properties and general process efficiency. The reactors and associated equipment are usually pre-treated to ensure proper reaction rates and catalyst performance. The reaction is usually conducted under inert atmosphere, where the catalyst system and feed components will not be in contact with any catalyst deactivator or poison which is usually polar oxygen, nitrogen, sulfur or acetylenic compounds.

One or more reactors in series or in parallel may be used in the present invention. The metallocene compound, activator and when required, co-activator, may be delivered as a solution or slurry in a solvent or in the alpha-olefin feed stream, either separately to the reactor, activated in-line just prior to the reactor, or preactivated and pumped as an activated solution or slurry to the reactor. Polymerizations/oligomerization are carried out in either single reactor operation, in which monomer, or several monomers, catalyst/activator/co-activator, optional scavenger, and optional modifiers are added continuously to a single reactor or in series reactor operation, in which the above components are added to each of two or more reactors connected in series. The catalyst system components can be added to the first reactor in the series. The catalyst system component may also be added to both reactors, with one component being added to first reaction and another component to other reactors. Preferably, the metallocene compound is activated in the reactor in the presence of olefin. Alternatively, the metallocene compound such as the dichloride form of the metallocene compounds is pre-treated with alkylaluminum reagents, especially, triisobutylaluminum, tri-n-hexylaluminum and/or tri-n-octylaluminum, followed by charging into the reactor containing other catalyst system component and the feed olefins, or followed by pre-activation with the other catalyst system component to give the fully activated catalyst, which is then fed into the reactor containing feed olefins. In another alternative, the pre-catalyst metallocene is mixed with the activator and/or the co-activator and this activated catalyst is then charged into reactor, together with feed olefin stream containing some scavenger or co-activator. In another alternative, the whole or part of the co-activator is pre-mixed with the feed olefins and charged into the reactor at the same time as the other catalyst solution containing metallocene and activators and/or co-activator.

The catalyst compositions can be used individually or can be mixed with other known polymerization catalysts to prepare polymer or oligomer blends. Monomer and catalyst selection allows polymer or oligomer blend preparation under conditions analogous to those using individual catalysts. Polymers having increased MWD are available from polymers made with mixed catalyst systems and can thus be achieved. Mixed catalyst can comprise two or more metallocene compounds and or two or more activators.

Preferably ethylene is present in the feed at 10 mol % or less, preferably 0.5 to 8 moles %, preferably 0.5 to 5 mol %, preferably from 1 to 3 mol %.

The PAO's described herein can also be produced in homogeneous solution processes. Generally this involves polymerization or oligomerization in a continuous reactor in which the polymer formed and the starting monomer and catalyst materials supplied, are agitated to reduce or avoid concentration or temperature gradients. Temperature control in the reactor is generally obtained by balancing the heat of polymerization and with reactor cooling by reactor jackets or cooling coils or a cooled side-stream of reactant to cool the contents of the reactor, auto refrigeration, pre-chilled feeds, vaporization of liquid medium (diluent, monomers or solvent) or combinations of the above. Adiabatic reactors with pre-chilled feeds may also be used. The reactor temperature depends on the catalyst used and the product desired. Higher temperatures tend to give lower molecular weights and lower temperatures tend to give higher molecular weights, however this is not a hard and fast rule. In general, the reactor temperature preferably can vary between about 0° C. and about 300° C., more preferably from about 10° C. to about 230° C., and most preferably from about 25° C. to about 200° C. Usually, it is important to control the reaction temperature as pre-determined. In order to produce fluids with narrow molecular distribution, such as to promote the highest possible shear stability, it is useful to control the reaction temperature to obtain minimum of temperature fluctuation in the reactor or over the course of the reaction time. If multiple reactors are used in series or in parallel, it is useful to keep the temperature constant in a pre-determined value to minimize any broadening of molecular weight distribution. In order to produce fluids with broad molecular weight distribution, one can adjust the reaction temperature swing or fluctuation, or as in series operation, the second reactor temperature is preferably higher than the first reactor temperature. In parallel reactor operation, the temperatures of the two reactors are independent. Or one can use two types of metallocene catalysts.

The pressure in any reactor used herein can vary from about 0.1 atmosphere to 100 atmosphere (1.5 psi to 1500 psi), preferably from 0.5 bar to 75 atm (8 psi-1125 psi), most preferably from 1.0 to 50 atm (15 psi to 750 psi). The reaction can be carried out under the atmosphere of nitrogen or with some hydrogen. Sometimes a small amount of hydrogen is added to the reactor to improve the catalyst. The amount of hydrogen is preferred to keep at such a level to improve catalyst productivity, but not induce any hydrogenation of olefins, especially the feed alpha-olefins because the conversion of alpha-olefins into saturated paraffins is very detrimental to the efficiency of the process. The amount of hydrogen partial pressure is preferred to be kept low, less than 50 psi, preferably less than 25 psi, preferably less than 10 psi, preferably less than 5 psi. Preferably the concentration of hydrogen in the reactant phase is less than 10,000 ppm, 100 ppm, preferably less than 50 ppm, preferably less than 10 ppm. In a particularly preferred embodiment in any of the process described herein the concentration of hydrogen in the reactor is kept at a partial pressure of preferably 50 psi (345 kPa) or less, preferably 10 psi (69 kPa) or less. Alternately, in any process described herein hydrogen, if present, is present in the reactor and or feed at 10,000 ppm or less, preferably 1000 ppm or less by weight, preferably 750 ppm or less, preferably 500 ppm or less, preferably 250 ppm or less, preferably 100 ppm or less, preferably 50 ppm or less, preferably 25 ppm or less.

The reaction time or reactor residence time can depend on the catalyst used, the amount of catalyst used, and the desired conversion level. Different metallocene compounds have different activities. Usually, a higher degree of alkyl substitution on the Cp ring, or bridging improves catalyst productivity. High amount of catalyst loading tends to gives high conversion at short reaction time. However, high amount of catalyst usage make the production process uneconomical and difficult to manage the reaction heat or to control the reaction temperature. Therefore, it is useful to choose a catalyst with maximum catalyst productivity to minimize the amount of metallocene and the amount of activators needed. When the catalyst system is metallocene plus methylalumoxane, the range of methylalumoxane used can be in the range of 0.1 milligram (mg) to 500 mg/g of alpha-olefin feed. A more preferred range is from 0.05 mg to 10 mg/g of alpha-olefin feed. Furthermore, the molar ratios of the aluminum to metallocene (Al/M molar ration) can range from 2 to 4000, preferably 10 to 2000, more preferably 50 to 1000, preferably 100 to 500. When the catalyst system is metallocene plus a Lewis Acid or an ionic promoter with NCA component, the metallocene use can be in the range of 0.01 microgram to 500 micrograms of metallocene component/gram of alpha-olefin feed. A preferred range is from 0.1 microgram to 100 microgram of metallocene component per gram of alpha-olefin feed. Furthermore, the molar ratio of the NCA activator to metallocene can be in the range from 0.1 to 10, preferably 0.5 to 5, preferably 0.5 to 3. If a co-activator of alkylaluminum compound is used, the molar ratio of the Al to metallocene can be in the range from 1 to 1000, preferably 2 to 500, preferably 4 to 400.

Typically one prefers to have the highest possible conversion (close to 100%) of feed alpha-olefin in shortest possible reaction time. However, in CSTR operation, sometimes it is beneficial to run the reaction at an optimum conversion, which can be less than 100% conversion, but preferably close to 100%. There are also occasions, when partial conversion is more desirable when the narrowest possible PDI of the product is desirable because partial conversion can avoid a PDI broadening effect. If the reaction is conducted to less than 100% conversion of the alpha-olefin, the unreacted starting material after separation from other product and solvents/diluents can be recycled to increase the total process efficiency.

Desirable residence times for any process described herein are in the range from 1 minutes to 20 hours, typically 5 minutes to 10 hours.

Each of these processes may also be employed in single reactor, parallel or series reactor configurations. The liquid processes comprise contacting olefin monomers with the above described catalyst system in a suitable diluent or solvent and allowing said monomers to react for a sufficient time to produce the desired polymers or oligomers. Hydrocarbon solvents both aliphatic and aromatic are suitable. Aromatics such as toluene, xylenes, ethylbenzene, propylbenzene, cumene, t-butylbenzene are suitable. Alkanes, such as hexane, heptane, pentane, isopentane, and octane, Norpar® or Isopar® solvents from ExxonMobil Chemical Company in Houston, Tex. are also suitable. Generally, toluene is most suitable to dissolve catalyst system components. Norpar®, Isopar® solvent or hexanes are preferred as reaction diluents. Oftentimes, a mixture of toluene and Norpar® or Isopar® is used as diluent or solvent.

The process can be carried out in a continuous stirred tank reactor or plug flow reactor, or more than one reactor operated in series or parallel. These reactors may have or may not have internal cooling and the monomer feed may or may not be refrigerated. See the general disclosure of U.S. Pat. No. 5,705,577 for general process conditions.

When a solid supported catalyst is used for the conversion, a slurry polymerization/oligomerization process generally operates in the similar temperature, pressure and residence time range as described previously. In a slurry polymerization or oligomerization, a suspension of solid catalyst, promoters, monomer and comonomers are added. The suspension including diluent is intermittently or continuously removed from the reactor. The catalyst is then separated from the product by filtration, centrifuge or settlement. The fluid is then distilled to remove solvent, any unreacted components and light product. A portion or all of the solvent and unreacted component or light components can be recycled for reuse.

If the catalyst used is un-supported, is a solution catalyst, when the reaction is complete or when the product is withdrawn from the reactor (such as in a CSTR), the product may still contain soluble, suspended or mixed catalyst system components. These components are preferably deactivated or removed. Any of the usual catalyst deactivation methods or aqueous wash methods can be used to remove the catalyst system component. Typically, the reaction is deactivated by addition of stoichiometric amount or excess of air, moisture, alcohol, isopropanol, etc. The mixture is then washed with dilute sodium hydroxide or with water to remove catalyst system components. The residual organic layer is then subjected to distillation to remove solvent, which can be recycled for reuse. The distillation can further remove any light reaction product from C18 and less. These light components can be used as diluent for further reaction. Or they can be used as olefinic raw material for other chemical synthesis, as these light olefin product have vinylidene unsaturation, most suitable for further functionalization to convert in high performance fluids. Or these light olefin products can be hydrogenated to be used as high quality paraffinic solvents.

Polymerization or oligomerization in absence of hydrogen is also advantageous to provide polymers or oligomers with high degree of unsaturated double bonds. These double bonds can be easily converted into functionalized fluids with multiple performance features. Examples for converting these polymers with MW greater than 300 can be found in preparation of ashless dispersants, by reacting the polymers with maleic anhydride to give PAO-succinic anhydride which can then reacted with amines, alcohols, polyether alcohols to convert into dispersants. Examples for such conversion can be found in the book "Lubricant Additives: Chemistry and Application," ed. By Leslie R. Rudnick, p. 143-170.

Desirably, in the process of the present disclosure, due to the structure features of the metallocene compound, the polymerization reaction mixture existing the polymerization reactor typically comprises residual olefin monomer feed, oligomers including vinylidenes, tri-substituted vinylenes, optionally 1,2-di-substituted vinylenes, and optionally vinyls, optionally solvents, and components derived from the catalyst system.

The polymerization reaction mixture is then typically quenched by the addition of a quenching agent such as water, $CO_2$, methanol, ethanol, mixtures thereof, and the like. Subsequently, the polymerization reaction mixture is separated to remove the residual monomer, which can be recycled to the polymerization reactor. Monomer removal can be carried out by means such as flashing under vacuum, distillation, or extraction. The resultant mixture is an unsaturated PAO product comprising vinylidenes, tri-substituted vinylenes, optionally 1,2-di-substituted vinylenes, and optionally vinyls.

The unsaturated PAO product desirably comprises vinylidenes and tri-substituted vinylenes at a high concentration, desirably in the range from c1 to c2 mol % in total, where c1 and c2 can be, independently, 50, 55, 60, 65, 70, 75, 80, 85, 90, 95, 98, based on the total moles of vinyls, vinylidenes, 1,2-di-substituted vinylenes, and tri-substituted vinylenes, as long as c1<c2. Preferably, c1=60, c2=90. More preferably, c1=70, c2=80. The high concentrations of vinylidenes and tri-substituted vinylenes are achieved partly by the unique structure of the metallocene compound used in the catalyst system. It is known that vinylidenes and tri-substituted vinylenes are more reactive than 1,2-di-substituted vinylenes when reacted with many functionalizing agents. Thus, the high concentration of vinylidenes and tri-substituted vinylenes in the unsaturated PAO product of the present disclosure is particularly advantageous if the unsaturated PAO product is used as intermediates for making functionalized olefins.

The unsaturated PAO product desirably contains 1,2-di-substituted vinylenes at a low concentration in the range from c5 to c6 mol %, based on the total moles of vinyls, vinylidenes, 1,2-di-substituted vinylenes, and tri-substituted vinylenes in the unsaturated PAO product, where c5 and c6 can be 0, 0.5, 1, 2, 3, 4, 5, 6, 7, 8, 9, 10, 11, as long as c5<c6. Preferably c5=0, c6=8. More preferably c5=0, c6=5. Such low concentration of 1,2-di-substituted vinylenes in the unsaturated PAO product is achieved by the low selectivity toward these olefins in the polymerization reactions, which is enabled again by the unique structure of the metallocene compound in the catalyst system used in the polymerization reaction.

Between the vinylidenes and tri-substituted vinylenes in the unsaturated PAO product of the present disclosure, vinylidenes tend to have a higher concentration than the tri-substituted vinylenes. Desirably, in the unsaturated PAO product of the present disclosure, the concentration of vinylidenes can range from c3 to c4 mol %, based on the total moles of the vinyls, vinylidenes, 1,2-di-substituted vinylenes, and tri-substituted vinylenes, where c3 and c4 can be, independently, 45, 50, 55, 60, 65, 70, 75, 80, 85, 90, as long as c3<c4. Preferably c3=50, c4=75. More preferably c3=55, c4=70. It has been found that, a non-coordinating anion with a large molecular size (e.g., D9 (dimethylanilinium tetrakisperfluoronapthylborate)) tends to result in higher selectivity toward vinyls and a lower selectivity toward vinylidenes compared to non-coordinating anions with a small molecular size (e.g., D4 (dimethylanilinium tetrakisperfluorophenylborate)) when used as the activator for the same metallocene compound of the present disclosure.

When the metallocene compound used in the catalyst system has both $R^5$ and $R^8$ being not hydrogen, then the process of the present disclosure tends to produce vinyls at a very low concentration, e.g., from c7 to c8 mol %, based on the total moles of vinyls, vinylidenes, 1,2-di-substituted vinylenes, and tri-substituted vinylenes in the unsaturated PAO product, where c7 and c8 can be 0, 0.5, 1, 2, 3, 4, 5, 6, 7, 8, 9, 10, as long as c7<c8. Preferably c7=0, c8=8. More preferably c7=0, c8=5. Without intending to be bound by a particular theory, it is believed that the substitution at $R^5$ and $R^8$ next to the bridge causes space hindrance that prevents the production of vinyl chain ends, hence a low selectivity toward vinyls. Nonetheless, the selectivity toward 1,2-di-substituted vinylenes typically remains very low as described above.

When the metallocene compound used in the catalyst system has at least one of $R^5$ and $R^8$ being hydrogen, then the process of the present disclosure can produce vinyls at a relatively high concentration, e.g., from c9 to c10 mol %, based on the total moles of vinyls, vinylidenes, 1,2-di-substituted vinylenes, and tri-substituted vinylenes in the unsaturated PAO product, where c9 and c10 can be 12, 14, 15, 16, 18, 20, 22, 24, 25, 26, 28, 30, 32, 34, 35, 36, 38, 40, as long as c9<c10. Preferably c9=15, c10=30. More preferably c9=15, c10=25. Without intending to be bound by a particular theory, it is believed that the presence of hydrogen one or both of the location of $R^5$ and $R^8$ next to the bridging group -BG- gives rise to sufficient space favoring production of vinyl chain ends, hence high selectivity toward vinyls at the expense of selectivity toward vinylidenes and tri-substituted vinylenes. Nonetheless, the selectivity toward 1,2-di-substituted vinylenes typically remains very low as described above.

The unsaturated PAO product obtained immediately after monomer removal can contain dimers, trimers, tetramers, pentamers, and even oligomers with a higher degree of polymerization. Extraction or fractionation may be carried out to separate the product into multiple fractions with differing boiling point ranges, corresponding to differing molecular weight range and differing degree of polymerization. For example, dimers can be separated out as a low-viscosity, low boiling point fraction as one grade of product, and the residual material may be used as another unsaturated PAO product grade.

V.4 Hydrogenation

At least a portion of the unsaturated PAO product can be hydrogenated to obtain an at least partly saturated PAO product. The unsaturated PAO product is preferably treated to reduce heteroatom-containing compounds to less than 600 ppm, and then contacted with hydrogen and a hydrogenation catalyst to produce a at least partly saturated, hydrogenated PAO product. The hydrogenated PAO product desirably has a bromine number less than 2.0, more desirably less than 1.8. Preferably the hydrogenation catalyst is selected from the group consisting of supported Group 7, 8, 9, and 10 metals, preferably the hydrogenation catalyst selected from the group consisting of one or more of Ni, Pd, Pt, Co, Rh, Fe, Ru, Os, Cr, Mo, and W, supported on silica, alumina, clay, titania, zirconia, or mixed metal oxide supports. A preferred hydrogenation catalyst is nickel supported on kieselguhr, or platinum or palladium supported on alumina, or cobalt-molybdenum supported on alumina. Preferably, a high nickel content catalyst, such as 60% Ni on Kieselguhr catalyst can be used, or a supported catalyst with high amount of Co—Mo loading. Alternately, the hydrogenation catalyst can be nickel supported on kieselguhr, silica, alumina, clay or silica-alumina.

Preferably the polyalpha-olefin is contacted with hydrogen and a hydrogenation catalyst at a temperature from 25 to 350° C., preferably 100 to 300° C. Preferably the polyalpha-olefin is contacted with hydrogen and a hydrogenation catalyst for a time period from 5 minutes to 100 hours, preferably from 5 minutes to 24 hours. Preferably the unsaturated PAO product is contacted with hydrogen and a hydrogenation catalyst at a hydrogen pressure of from 25 psi to 2500 psi, preferably from 100 to 2000 psi. Further information on hydrogenation of unsaturated PAO products can be found in U.S. Pat. No. 5,573,657 and "Lubricant Base Oil Hydrogen Refining Processes" (page 119 to 152 of Lubricant Base Oil and Wax Processing, by Avilino Sequeira, Jr., Marcel Dekker, Inc., NY, 1994.

This hydrogenation process can be accomplished in a slurry reactor in a batch operation or in a continuous stirred tank reactor (CSTR), where the catalyst in 0.001 wt % to 20 wt % of the unsaturated PAO feed or preferably 0.01 to 10 wt %, hydrogen and the uPAOs are continuously added to the reactor to allow for certain residence time, usually 5 minutes to 10 hours to allow substantially complete hydrogenation of the unsaturated olefins. The amount of catalyst added is usually very small just to compensate for the catalyst deactivation. The catalyst and hydrogenated PAO can be continuously withdrawn from the reactor. The product mixture can be filtered, centrifuged or settled to remove the solid hydrogenation catalyst. The catalyst can be regenerated and reused. The hydrogenated PAO can be used as is or further distilled or fractionated to the right component if necessary. In some cases, when the hydrogenation catalyst show no catalyst deactivation over long term operation, the stir tank hydrogenation process can be carried out in a manner where a fixed amount of catalyst is maintained in the reactor, usually 0.1 wt % to 10% of the total reactant, and only hydrogen and PAO feed are continuously added at certain feed rate and only hydrogenated PAO was withdrawn from the reactor.

The hydrogenation process can also be accomplished by a fixed bed process, in which the solid catalyst can be packed inside a tubular reactor and heated to reactor temperature. Hydrogen and PAO feed can be fed through the reactor simultaneously from the top or bottom or counter-currentwise to maximize the contact between hydrogen, PAO and catalyst and to allow best heat management. The feed rate of the PAO and hydrogen are adjusted to give proper residence time to allow complete hydrogenation of the unsaturated PAOs in the feed. The hydrogenated PAO fluid can be used as is or further distilled or fractionated to give the right component, if necessary. Usually, the finished hydrogenated PAO product can have a bromine number less than 2.

VI.1 The Lubricant Base Stock of the Present Disclosure

The unsaturated PAO products and the hydrogenated PAO products of the present disclosure, advantageously obtainable by using the processes of the present disclosure, can be used as a base stock for lubricating oil compositions. Preferably the hydrogenated PAO product having a bromine number no greater than 2.0 is used as a lubricating oil base stock. The base stock can be at any viscosity grade useful for any particular lubricating oil composition. The base stocks of the present disclosure can be blended with each other, other API Group I, II, III, IV, or V base stocks, lubricating additive packages, and the like, to form a lubricating oil composition. "Lubricating oil," "lubricating oil composition," and "lubricant" are used herein interchangeably. The lubricants can be internal combustion engine oils, gas turbine oils, automobile drive line fluids, power transfer fluids (hydraulic oil, e.g.), processing oils, heat transfer oils (e.g., transformer oils), industrial lubricants, gear box lubricants, and the like.

The present disclosure is further illustrated by the following non-limiting examples.

EXAMPLES

Part A

Syntheses of Metallocene Compounds

All syntheses were carried out in an $N_2$ purged dry box using standard air sensitive procedures. Ligands (such as substituted or unsubstituted Cp, indene, 9H-fluorene) used in the synthesis are commercially available from reagent suppliers such as Sigma Aldrich (www.sigmaaldrich.com) and Boulder Scientific Company (www.bouldersci.com). Lithiated ligands can be made by reacting the ligands with n-BuLi as illustrated and exemplified in U.S. Patent Application Publication No. 2013/0023633 A1. Ligands bridged by the bridging groups can be synthesized by reacting the lithiated ligands and $SiMe_2Cl_2$, as illustrated and exemplified in U.S. Publication No. 2013/0023633 A1. In the synthesis processes, to the extent two stereo isomers exist in any of the metallocene compounds, a mixture of the two isomers are produced. Therefore, even if the molecular formula shown below appears to represent a single isomer, interpretation thereof should mean a mixture of multiple isomers possible. For example, even though the structure of compound I-1 below appears to show an isomer in which the phenyl ring annelated to the upper Cp ring is on the left side of a plane passing through the centers of the two Cp rings, the Zr atom and the —$SiMe_2$— bridging group, the Compound I-1 should be interpreted to also include, in addition to the isomer illustrated in Example A1, the isomer in which the phenyl ring annelated to the upper Cp ring is on the right side of the plane shown as follows:

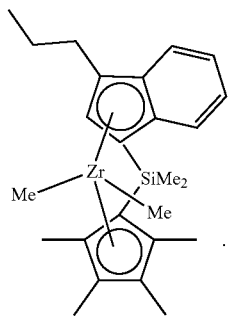

Example A1

Synthesis of Metallocene Compound I-1: $Me_2Si$ $(Me_4Cp)(3\text{-Prind})ZrMe_2$

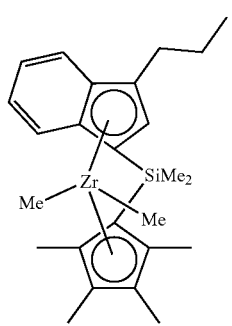

I-1

The solid dilithio salt (1.22 g, 2.6 mmol) of $Me_2Si$ $(Me_4Cp)(3\text{-Prind})Li_2$ was slurried in $Et_2O$ (50 ml) and reacted with $ZrCl_4$ (0.613 g, 2.6 mmol). After stirring for 4 hours, the reaction was complete as determined by crude $^1H$ NMR. The reaction was filtered and the solids were washed by dichloromethane 3 times. All solvents were removed in vacuum, and the off-green solid (1.0 g) was collected. The product was re-slurried in toluene (20 ml) and reacted with MeMgI (1.75 ml, 3 M in $Et_2O$). The reaction was stirred at 68° C. for 4 hours. Crude $^1H$ NMR showed that reaction was complete. The reaction mixture was cooled to room temperature and 1,4-dioxane (0.6 ml) was added. The mixture was stirred for 20 min and the all solids were removed by filtration and washed by dichloromethane. After removal of all solvents, solid (0.82 g) was isolated as the final methylated product, Me$_2$Si(Me$_4$Cp)(3-PrInd)ZrMe$_2$, which was analyzed by $^1$H NMR (CD$_2$Cl$_2$, 400 MHz): δ 7.58 (dt, J=8.5, 1.1 Hz, 1H), 7.29 (dt, J=8.6, 1.0 Hz, 1H), 7.20 (ddd, J=8.5, 6.6, 1.0 Hz, 1H), 6.92 (ddd, J=8.6, 6.6, 1.1 Hz, 1H), 5.43 (s, 1H), 3.10-2.85 (m, 1H), 2.56 (ddd, J=14.4, 9.1, 6.4 Hz, 1H), 1.88 (s, 6H), 1.78 (s, 3H), 1.76-1.66 (m, 4H), 1.64-1.49 (m, 1H), 0.96 (t, J=7.4 Hz, 3H), 0.90 (s, 3H), 0.68 (s, 3H), −0.81 (S, 3H), −1.96 (S, 3H).

Example A2

Synthesis of Metallocene Compound I-2: Me$_2$Si(Me$_4$Cp)(3-PrInd)HfMe$_2$

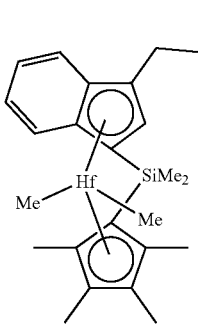

I-2

3-propylindenyl lithium (1.50 g, 9.1 mmol) was dissolved in THF (30 ml) and reacted with CpMe$_4$HMe$_2$SiCl (1.96 g, 9.1 mmol). The reaction was stirred overnight at room temperature. Crude $^1$H NMR showed that the reaction was complete. All volatiles were removed and the crude product was re-slurried into pentane. The crude product was filtered through Celite. All volatiles were then removed in vacuum. Product was isolated as clear oil and was dissolved in Et$_2$O (20 ml). 11M n-Bu-Li in hexanes (1.7 ml, 18.3 mmol) was then slowly added. The reaction was stirred for 3 hours at room temperature. Crude $^1$H NMR showed that the reaction was complete. Pentane (40 ml) was added to the reaction mixture and it was stirred for 30 min. The product was isolated by filtration as white solid (2.1 g), which was washed by pentane twice during filtration. The solid dilithiated product was slurried in Et$_2$O (50 ml) and reacted with HfCl$_4$ (1.35 g, 4 mmol). After stirring for 4 hours, the reaction was complete as determined by crude $^1$H NMR. The reaction was filtered and the solids were washed by dichloromethane 3 times. Organic solutions were combined and all volatiles were removed in vacuum. And the product was collected as yellow solid (1.64 g), which was then re-slurried in toluene (20 ml) and reacted with MeMgI (1.7 ml, 3 M in Et$_2$O). The reaction was stirred at 65° C. for 16 hours. Crude $^1$H NMR showed that reaction was complete. The reaction mixture was cooled to room temperature and 1,4-dioxane (1 ml) was added. The mixture was stirred for 20 min and the all solids were removed by filtration and washed by dichloromethane. After removal of all solvents, bright yellow solid (1.2 g) was isolated as the final methylated product, Me$_2$Si(CpMe$_4$)(3-PrInd)HfMe$_2$, which was analyzed by $^1$H NMR (CD$_2$Cl$_2$, 400 MHz): δ 7.59 (dt, J=8.6, 1.0 Hz, 1H), 7.33 (dt, J=8.7, 1.0 Hz, 1H), 7.22 (ddd, J=8.6, 6.6, 1.0 Hz, 1H), 6.96 (ddd, J=8.7, 6.6, 1.2 Hz, 1H), 5.43 (s, 1H), 2.95 (ddd, J=14.6, 9.1, 5.9 Hz, 1H), 2.54 (ddd, J=14.3, 9.1, 6.4 Hz, 1H), 1.92 (s, 3H), 1.91 (s, 3H), 1.85 (s, 3H), 1.83 (s, 3H), 1.82-1.66 (m, 1H), 1.64-1.51 (m, 1H), 0.98 (t, J=7.3 Hz, 3H), 0.94 (s, 3H), 0.72 (s, 3H), −0.97 (s, 3H), −2.11 (s, 3H).

Example A3

Synthesis of Metallocene Compound I-3: Me$_2$Si(CpMe$_4$)(3-PrCp)ZrMe$_2$

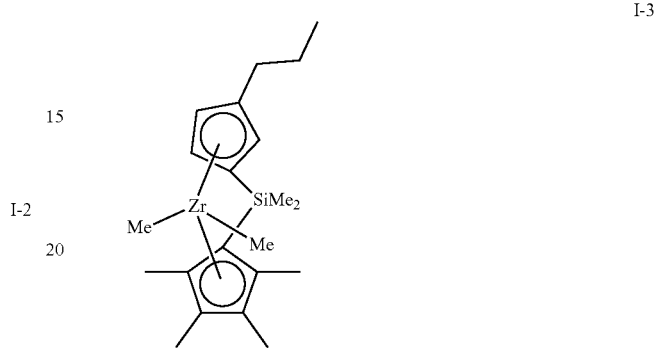

I-3

CpPrLi (8.2 g) was added to a solution of CpMe$_4$HSiMe$_2$Cl (15.5 g) in THF (200 mL) previously cooled to −30° C. The reaction was warmed to room temperature and analyzed by $^1$H NMR after 1 hour at room temperature. The volatiles were removed and the crude reaction mixture extracted with pentane (2×50 mL). The extracts were reduced in vacuum to yield a yellowish liquid (20.2 g). All was dissolved in Et$_2$O (200 mL) and reacted with n-Bu-Li (11.5 g, 11 M in hexanes). After 1 hour the volatiles were removed and the solid dilithio salt was with hexane (2×50 mL) and dried (20.2 g). ZrCl$_4$ (15.0 g) was slurried in 300 mL Et$_2$O and slowly the dilithio ligand was added at room temperature. An aliquot at 20 minutes after addition shows complete reaction. The volatiles were stripped to about 50 mL and the light yellow product filtered and dried in vacuum (15.6 g). All was dissolved in 200 mL toluene and reacted with MeMgI (30.4 g, 3 M) for 16 hour. Dioxane (10 mL) was added and the reaction filtered and reduced in vacuum. The product was extracted with hexane (2×50 mL) and filtered and reduced to yield an off-white solid product (10.1 g) which was analyzed by $^1$H NMR (CD$_2$Cl$_2$, 400 MHz). NMR spectrum confirmed structure.

Example A4

Synthesis of Metallocene Compound I-4: Me$_2$Si(CpMe$_4$)(3-MeCp)ZrMe$_2$

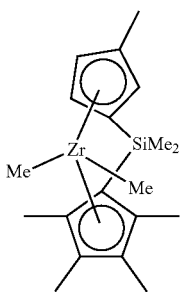

I-4

Me$_2$Si(CpMe$_4$)(3-MeCp)ZrCl$_2$ (Compound I-5 below) (5.0 g) was slurried in Et$_2$O (80 mL) and reacted with 11 g MeMgI (3 M in Et$_2$O). After 2 hours, the volatiles were removed and the crude extracted with hexane (2×40 mL). The volatiles were removed to yield a white solid (3.1 g). $^1$H NMR (400 MHz, CD$_2$Cl$_2$) 6.52 (m), 5.46 (m), 5.18 (m), 2.25 (s), 2.02 (s), 2.01 (s), 1.73 (s), 1.62 (s), 0.55 (s), 0.53 (s), −0.75 (s), −0.79 (s).

Example A5

Synthesis of Metallocene Compound I-5: Me$_2$Si(CpMe$_4$)(3-MeCp)ZrCl$_2$

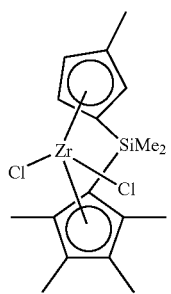

I-5

This compound can be synthesized using the ligand (CpMe4HLi) in the reaction with Me$_2$SiCl$_2$ first, followed by the reaction of (CpH4MeLi) with the first reaction product, CpMe$_4$H—SiMe$_2$Cl to yield the neutral ligand. Further synthetic steps are carried out using the synthesis approach similar to that of Example A3.

Example A6

Synthesis of Metallocene Compound I-6: Me$_2$Si(3-PrCp)(C$_{13}$H$_8$)ZrMe$_2$

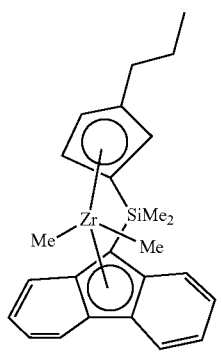

I-6

C$_{13}$H$_9$SiMe$_2$Cl (7.8 g, 30.2 mmol) was dissolved in THF (60 mL) and reacted with CpPrLi (3.4 g) for 1 hour. The volatiles were removed and the crude reaction was extracted with hexane (2×50 mL) and filtered through a glass frit. The extracts were reduced to a yellowish oil (8.5 g). All was dissolved in Et$_2$O (60 mL) and reacted with n-Bu-Li (4.2 g, 10 M). After 1 hour the volatiles were removed and the crude washed with hexane (4×100 mL) to yield an orange solid (11.2 g). Some of the dilithio ligand (6.0 g) was dissolved in Et$_2$O (100 mL) and reacted with ZrCl$_4$ (3.0 g). After 2 hours, the dichloride was isolated by filtration to yield an orange solid (4.8 g). Some (3.2 g) slurried in Et$_2$O (80 mL) and reacted with MeMgI (5.4 g, 3 M) for 16 hours. The crude reaction was extracted with toluene to which dimethoxyethane (ca 5 mL) had been added. The extract was cooled to −35° C. and the product was obtained as a solid (0.57 g). $^1$H NMR (CD$_2$Cl$_2$, 500 MHz); 8.08 (m), 7.25 (m), 7.07 (t), 6.06 (t), 5.35 (t), 5.17 (t), 2.12 (m), 1.36 (m), 0.79 (d, SiMe$_2$), 0.77 (t), −1.78 (s), −1.83 (s).

Example A7

Synthesis of Metallocene Compound I-7: Me$_2$Si(Me$_4$Cp)(3-Pr-2-Me-Ind)HfMe$_2$

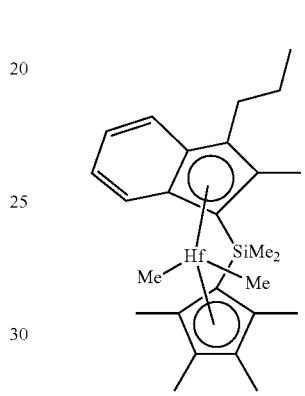

I-7

This compound can be synthesized using commercially available ligands and the approach described in Example A1 for synthesizing Compound I-1.

Example A8

Synthesis of Metallocene Compound I-8: Me$_2$Si(CpMe$_4$)(3-BzCp)ZrMe$_2$

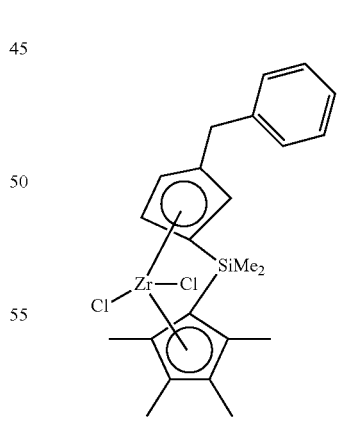

I-8

CpMe$_4$HSiMe$_2$Cl (5.0 g, 23 mmol) was dissolved in THF (100 mL) and reacted with BzCpLi (3.8 g, 23 mmol). After 1 hour the reaction was complete as determined by $^1$H NMR. All volatiles were removed and the residue extracted with pentane (50 mL). The extraction was filtered and reduced in vacuum. It was dissolved in Et$_2$O (50 mL) and was reacted with 3.4 g 11 M n-Bu-Li. After 1 hour, pentane (100 mL)

was added and the solvents were decanted. The remaining solid dilithiated product was washed with more pentane and dried until a solid was obtained. All was slurried in Et$_2$O (80 mL) and reacted with ZrCl$_4$ (4.0 g, 17 mmol). After 1 hour the crude reaction mixture was filtered through a plastic frit and the solution allowed to remain uncovered to induce precipitation. After 2 days an off-white solid was filtered and dried (4.2 g). All was slurried in Et$_2$O (50 mL) and reacted with MeMgI (6.8 g, 3 M in Et$_2$O). After 1 hour the reaction was complete as determined by $^1$H NMR and the volatiles were removed in vacuum. Toluene (50 mL) and dioxane (7 mL) were added to the crude reaction with stirring. The reaction was filtered through Celite and the extract reduced to a white solid product, Me$_2$Si(CpMe$_4$)(3-BzCp)ZrMe$_2$ (3.3 g), which was analyzed by $^1$H NMR (C$_6$D$_6$, 400 MHz).

Example A9

Synthesis of Metallocene Compound I-9: Me$_2$Si(CpMe$_4$)(3-(1-hexenyl)Cp)ZrMe$_2$

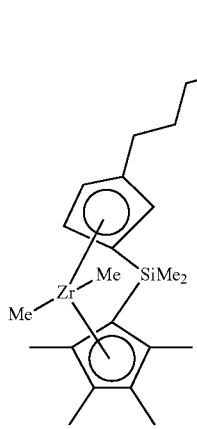

I-9

CpMg (49.4 g, 1.12 M, 62 mmol) was reacted with 6-bromo, 1-hexene (8.5 g) at reflux for 8 hours. All volatiles were removed in vacuum and the crude was extracted with pentane (2×100 mL). The extracts were deprotonated with n-Bu-Li (4.5 g, 11 M). THF (50 mL) was added to the reaction. After 16 hours the volatiles were removed and the waxy residue was washed with pentane and collected on a frit. Yield was 4.1 g. Some C$_p$C$_4$H$_8$CH=CH$_2$Li (1.7 g, 11 mmol) was reacted with CpMe$_4$HSiMe$_2$Cl (2.3 g) dissolved in THF (50 mL). After 16 hours the volatiles were removed and the crude reaction was extracted with pentane (2×50 mL). The reduced extracts were dissolved in Et$_2$O (60 mL) and reacted with n-Bu-Li (2.2 g, 11 M). After 2 hours, pentane (40 mL) was added and a white solid was filtered and washed with pentane and Et$_2$O (3×50 mL). The white dilithio ligand (3.4 g) was slurried in Et$_2$O (60 mL) and reacted with ZrCl$_4$ (2.0 g) for 1 hour. The reaction was filtered and reacted with MeMgI (7.2 g, 3 M). After 1 hour the reaction was analyzed by $^1$H NMR and was determined to be complete. The volatiles were reduced in vacuum and the crude product extracted with pentane (2×50 mL). The volatiles were removed to yield pure product as a clear liquid (3.2 g). The product was analyzed by $^1$H NMR (C$_6$D$_6$, 400 MHz); 6.59 (s, 1H), 5.75 (m, 1H), 5.32 (s, 1H), 5.13 (s, 1H), 4.98 (m, 2H), 2.66 (m, 2H), 1.97 (s, CpMe), 1.96 (s, CpMe), 1.69 (s, CpMe), 1.63 (s, CpMe) (multiplets due to overlapping hexenyl resonances in the "CpMe$_4$" region made integration difficult), 1.43 (m, 2H), 0.39 (s, 3H), 0.37 (s, 3H), −0.30 (s, 3H), −0.39 (s, 3H).

Example A10

Synthesis of Metallocene Compound I-10: Me$_2$Si(3-PrCp)$_2$ZrMe$_2$

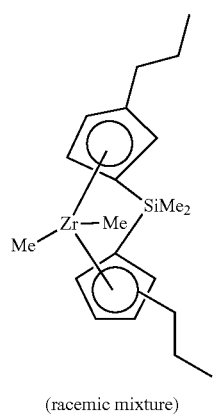

I-10

(racemic mixture)

CpPrLi (7.35 g) was dissolved in THF (150 mL), cooled to −35° C. and reacted with Me$_2$SiCl$_2$ (4.0 g). The crude reaction mixture was warmed to room temperature and stirred for 16 hours. The volatiles were removed and the crude reaction mixture extracted with pentane (2×40 mL). The filtrates were dissolved in Et$_2$O and reacted with n-Bu-Li (4.7 g, 11 M in hexane) slowly. The solid dilithio ligand was collected on a frit after 2 hours and washed with pentane. All (6.5 g) was slurried in Et$_2$O (200 mL) and reacted with ZrCl$_4$ (5.2 g). The reaction mixture was filtered and the filtrate reacted with MeMgI (13.6 g, 3 M) for 1 hour. The volatiles were removed and the crude reaction mixture extracted with pentane. The filtrate was and reduced to an oil (5.7 g). Analysis by $^1$H NMR (CD$_2$Cl$_2$, 400 MHz) showed the product to be a mixture of rac and meso isomers; 0.95, 0.92 (s, meso-SiMe$_2$), 0.93 (r-SiMe$_2$), 0.72, 0.66 (meso-ZrMe$_2$), 0.69 (r-ZrMe$_2$).

Example A11

Synthesis of Metallocene Compound I-11: Me$_2$Si(CpMe$_4$)(Pr(CH$_2$)$_4$Ind)HfMe$_2$

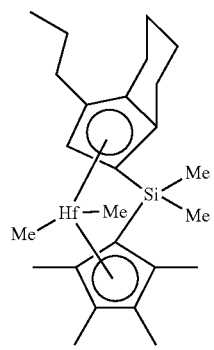

I-11

Me$_2$Si(Me$_4$Cp)(3-PrInd)HfCl$_2$ (1.64 g) was slurried in dichloromethane (20 ml) with catalytic amount of PtO$_2$ (0.13 g, 0.6 mmol). The mixture was transferred into the hydrogenation par bomb reactor. Take the reactor out of the nitrogen box and purge the reactor with hydrogen gas for 1 minute to remove most nitrogen and then the reactor was charged with hydrogen to 350 psi. The reaction was stirred at 40° C. for 24 hours. The reactor was then taken into the box and the pressure of the reactor was gently released. The black solid was filtered through celite and washed by dichloromethane. All volatiles were removed under vacuum. The crude product was slurried in Et$_2$O (15 ml) and small amount of pentane (~5 ml) was added. Off-white solid was filtered and dried (0.78 g). All was slurried in toluene (30 mL) and reacted with MeMgI (0.9 ml, 3 M in Et$_2$O). The reaction was stirred at 85° C. for 38 hours. Crude $^1$H NMR showed that reaction was completed. The reaction mixture was cooled to room temperature and 1,4-dioxane (1 ml) was added. The mixture was stirred for 20 min and the all solids were removed by filtration and washed by dichloromethane. After removal of all solvents, white solid (0.55 g) was isolated as the final methylated product, Me$_2$Si(CpMe$_4$)(n-Pr(CH$_2$)$_4$Ind)HfMe$_2$, which was analyzed by $^1$H NMR (CD$_2$Cl$_2$, 400 MHz): δ 4.82 (s, 1H), 2.80-2.51 (m, 3H), 2.45 (ddd, J=14.4, 9.7, 5.7 Hz, 1H), 2.31-2.10 (m, 2H), 2.05 (s, 3H), 1.96 (s, 3H), 1.84-1.67 (m, 6H), 1.65-1.48 (m, 2H), 1.48-1.34 (m, 1H), 0.96 (t, J=7.3 Hz, 3H), 0.68 (s, 3H), 0.59 (s, 3H), −0.91 (s, 3H), −1.06 (s, 3H).

Example A12

Synthesis of Metallocene Compound I-12: Me$_2$Si(CpMe$_4$)(n-Pr(CH$_2$)$_4$Ind)ZrMe$_2$

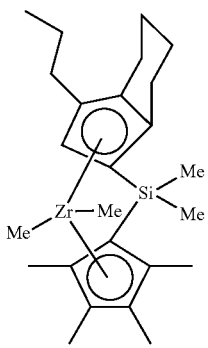

I-12

Me$_2$Si(CpMe$_4$)(PrInd)ZrCl$_2$ (1.25 g, 2.5 mmol) was slurried in dichloromethane (20 ml) with catalytic amount of PtO$_2$ (0.20 g, 0.8 mmol). The mixture was transferred into the hydrogenation par bomb reactor. The reactor, out of the nitrogen box, was purged the with hydrogen gas for 1 minute. The reaction was stirred at 40° C. for 24 hours. The reactor was then taken into the box and the pressure of the reactor was gently released. The black solid was filtered through celite and washed by dichloromethane. All volatiles were removed under vacuum. The crude product was stirred in Et$_2$O (15 ml). Pale green solid was filtered and collected as pure product. All solvents were then removed. The crude product was washed by cold Et$_2$O and then dried. The combined solid (0.58 g) was slurried in toluene (30 mL) and reacted with MeMgI (0.8 ml, 3 M in Et$_2$O). The reaction was stirred at 80° C. for 16 hours. Crude $^1$H NMR showed that reaction is complete. The reaction mixture was cooled to room temperature and 1,4-dioxane (0.6 ml) was added. The mixture was stirred for 20 min and the all solids were removed by filtration and washed by dichloromethane. After removal of all solvents, white solid (0.47 g) was isolated as the final methylated product, Me$_2$Si(CpMe$_4$)(Pr(CH$_2$)$_4$Ind)ZrMe$_2$, which was analyzed by $^1$H NMR (CD$_2$Cl$_2$, 400 MHz): δ 4.85 (s, 1H), 2.78-2.59 (m, 2H), 2.58-2.37 (m, 2H), 2.24 (ddd, J=14.4, 9.8, 6.0 Hz, 1H), 2.16-2.04 (m, 4H), 1.98 (s, 3H), 1.82 (s, 3H), 1.79-1.68 (m, 6H), 1.65-1.32 (m, 3H), 0.97 (t, J=7.3 Hz, 3H), 0.67 (s, 3H), 0.56 (s, 3H), −0.77 (s, 3H), −0.89 (s, 3H).

Example A13

Synthesis of Metallocene Compound I-13: Me$_2$Si(CpMe$_4$)(3-BzCp)ZrMe$_2$

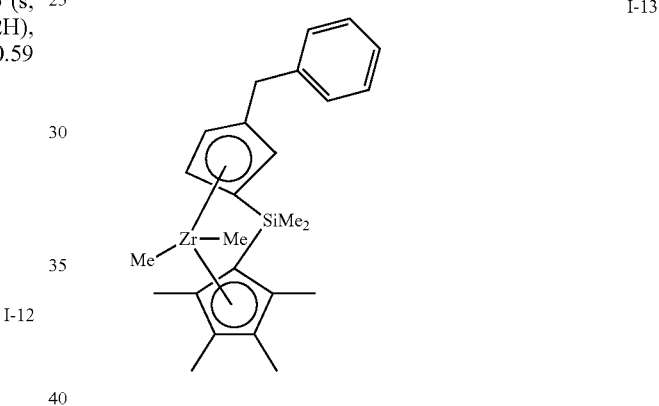

I-13

CpMe$_4$HSiMe$_2$Cl (5.0 g, 23 mmol) was dissolved in THF (100 mL) and reacted with BzCpLi (3.8 g, 23 mmol). After 1 hour the reaction was complete as determined by $^1$H NMR. All volatiles were removed and the residue extracted with pentane (50 mL). The extraction was filtered and reduced in vacuo. It was dissolved in Et$_2$O (50 mL) and was reacted with 3.4 g 11 M n-BuLi. After 1 hour, pentane (100 mL) was added and the solvents were decanted. The remaining solid dilithiated product was washed with more pentane and dried until a solid was obtained. All was slurried in Et$_2$O (80 mL) and reacted with ZrCl$_4$ (4.0 g, 17 mmol). After 1 hour the crude reaction mixture was filtered through a plastic frit and the solution allowed to remain uncovered to induce precipitation. After 2 days an off-white solid was filtered and dried (4.2 g). All was slurried in Et$_2$O (50 mL) and reacted with MeMgI (6.8 g, 3 M in Et$_2$O). After 1 hour the reaction was complete as determined by $^1$H NMR and the volatiles were removed in vacuo. Toluene (50 mL) and dioxane (7 mL) were added to the crude reaction with stirring. The reaction was filtered through Celite and the extract reduced to a white solid product, Me$_2$Si(CpMe$_4$)(3-BzCp)ZrMe$_2$ (3.3 g), which was analyzed by $^1$H NMR (C$_6$D$_6$, 400 MHz). The NMR spectrum confirmed the structure.

Example A14

Synthesis of Metallocene Compound X-2: (CpBz)₂ZrMe₂

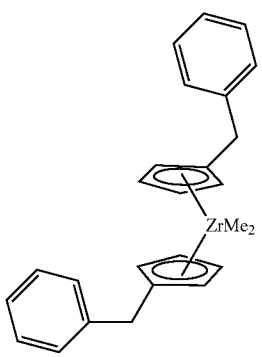

X-2

CpBzLi (2.0 g) was slurried in Et₂O (50 mL) and reacted with ZrCl₄ (1.6 g) at room temperature for 3 hr. A white solid was filtered and dried (2.1 g). All was slurried in Et₂O (40 mL) and reacted with MeMgI (4 g, 3.0 M) for 16 hr. The volatiles were removed and the crude extracted with hexane (2×30 mL). The volatiles were removed to yield the complex as a white solid (1.0 g). ¹H NMR (CD₂Cl₂, 400 MHz) δ 7.32-7.14 (m, 10H), 5.89 (t, J=2.9, 4H), 5.80 (t, J=2.6 Hz, 4H), 2.91-2.73 (m, 4H), −0.46 (s, 6H).

Example A15

Synthesis of Metallocene Compound X-5: Me₂Si(CpMe₃H)(Cp)ZrMe₂

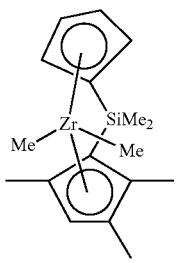

X-5

CpMe₃H₂Li (3.8 g) was added to a solution of Me₂SiCl₂ (25 g) in 100 mL pentane. After 3 days the reaction was filtered and the filtrate reduced to an oil (5.2 g). All was dissolved in THF (100 mL) and reacted with CpLi (1.8 g, Strem). The volatiles were removed and the crude reaction was extracted with pentane (2×30 mL). The pentane extracts were reacted with n-BuLi (4.2 g, 10 M). A white solid was collected. It was slurried in Et₂O (60 mL) and reacted with ZrCl₄ (3 g). A white solid was obtained after filtration (4.2 g). Me₂Si(CpMe₃H)(Cp)ZrCl₂ (3.1 g) was slurried in Et₂O (100 mL) and reacted with MeMgI (6.6 g, 3.0 M) for 16 hour. The volatiles were removed in vacuo and the crude was extracted with hexane (2×30 mL) and filtered through celite. The volatiles were removed to yield the product as a white solid (2.1 g). 1H-NMR spectrum confirmed the structure.

Example A16

Synthesis of Metallocene Compound X-6

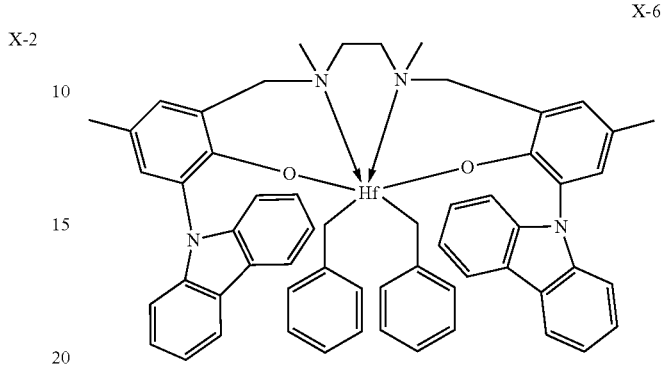

X-6

Description of synthesis of this compound can be found in U.S. Pat. No. 8,957,171 B2.

Example A17

Synthesis of Metallocene Compound X-7: Me₂Si(CpMe₄)(Cp)ZrMe₂

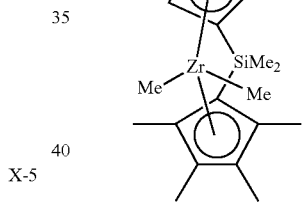

X-7

CpMe₄HLi (42 g) was slowly added to a solution of Me₂SiCl₂ (110 g) in THF (500 mL) at room temperature. After 16 hour the solvents and excess Me₂SiCl₂ are removed in vacuo. The crude is dissolved in THF (300 mL) and reacted with 130 g CpNa (2 M in THF) for 2 hrs. The volatiles are removed in vacuo and the crude extracted with pentane (2×50 mL). The oil was dissolved in THF and reacted with 26 g n-BuLi (10 M in hexanes) for 16 hr. A white solid was collected and washed with pentane. All was slurried in Et₂O (800 mL) and reacted with ZrCl₄ (43 g) slowly as the reaction is exothermic. The reaction was filtered and the light yellow material remaining on frit was extracted exhaustively with CH₂Cl₂. The volatiles were removed to yield 22.1 g of Me₂Si(CpMe₄)(Cp)ZrCl₂. The complex was analyzed by H NMR (400 MHz) in CD₂Cl₂. The ¹H-NMR spectrum confirmed the structure.

Part B

Oligomerization of 1-Decene Using Catalyst Systems Comprising Metallocene Compounds In all of the inventive examples and comparative examples in Part B, 1-decene was polymerized in the presence of an oligomerization catalyst system comprising a metallocene compound (MC), an activator (or co-catalyst) selected from D4 (dimethylanilinium tetrakisperfluorophenylborate), D9 (dimethylanilinium tetrakisperfluoronapthylborate), and methylaluminoxane (MAO), and tri-n-octylaluminum as the scavenger. The catalyst system components were dissolved in toluene, and then mixed with the 1-decene monomer and allowed to effect the oligomerization at a given reaction temperature. After 1 hour, the oligomerization reaction was quenched by a quenching agent, and the reaction mixture was flashed under vacuum to remove the residual unreacted monomer and lights to leave an unsaturated PAO product. The unsaturated PAO product is then analyzed to determine the distributions of vinylidenes ("Vd"), 1,2-di-substituted vinylenes ("Di"), tri-substituted vinylenes ("Tri"), and vinyls ("Vi"), and physical properties such as KV100, and the like. Conversions of the reactions were calculated from the total quantity of products made and the feed materials used.

The 1-decene monomer was purchased from SigmaAldrich and purified by passing through a basic Alumina column and dried over 3 Angstrom molecular sieves before use. D4 and D9 were purchased from Albemarle Corporation and used as received. Reaction solvents were purchased as anhydrous versions from Aldrich and dried with activated 3 Angstrom molecular sieves for at least 24 hours prior to use. MAO (methylalumoxane) was purchased from Albemarle Corporation as a 30 wt % solution in toluene.

The metallocene compounds used in all examples in Part B were synthesized as described above in Examples Part A or purchased from Boulder Scientific. The metallocene compounds not described in Part A are as follows:

TABLE II below shows inventive Examples 1-8, listing reaction conditions including identity of the metallocene compound, the NCA activator, the polymerization temperature, and the like, together with the distributions of the olefins in terms of mole percentages of each type, on the basis of the total moles of the four categories of olefins. Each example having the same catalyst system was repeated at three polymerization temperatures (60, 85, and 100° C.). All metallocene compounds used in Examples 1-6 have structures with the following commonalities: (i) the two Cp-rings are single-bridged; (ii) they all have one tetra-substituted Cp ring ligand, and the other Cp ring ligand has a 3-alkyl (methyl or n-propyl) substituent and an unsubstituted position adjacent to bridge. Data in TABLE II show that this pattern in the metallocene compounds resulted in high selectivity toward either vinylidenes or a high selectivity toward the combination of vinylidenes and tri-substituted vinylenes, and in general, a very low selectivity toward 1,2-di-substituted vinylenes.

The metallocene compound in Examples 7 (I-7) differs from those in Examples 1-6 in that all four carbon atoms on the two Cp rings next to the bridge are substituted by an alkyl group. Without intending to be bound by a particular theory, it is believed that the complete substitution next to the bridge causes the formation of vinyl chain ends while still minimizing the 1,2-di-substituted vinylene content, resulting in a low selectivity toward 1,2-di-substituted olefins and a much higher selectivity toward vinyls than those in Examples 1-5.

All inventive examples demonstrated very low selectivity toward 1,2-di-substituted vinylenes in the polymerization reaction. With the only exception of Example 6a, they all

| Compound | Compound Structure | Source |
|---|---|---|
| X-1 | 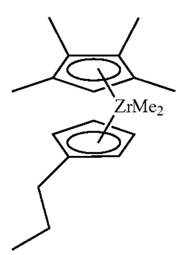 | Available from Albemarle Corporation |
| X-3 | 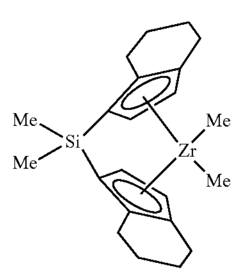 | Available from Albemarle Corporation |
| X-4 | | Available from Boulder Scientific Corporation | showed selectivity toward 1,2-di-substituted vinylenes lower than 10%. All inventive examples showed selectivity toward vinylidenes higher than 50%. Indeed, all inventive examples showed selectivity toward vinylidenes, tri-substituted vinylenes and vinyls combined higher than 90% except Example 6a. All Examples 1-6 showed vinylidene selectivity higher than 80%. All examples 1-5 showed selectivity toward vinylidenes and tri-substituted vinylenes combined higher than 90%. As such, the thus made uPAO product mixture is highly useful as intermediates for making functionalized PAO materials where the reactivity of vinylidenes and/or tri-substituted vinylenes are particularly desired.

TABLE III shows comparative examples C1 to C9, each repeated with the same catalyst system but at three different polymerization temperatures (60, 85, and 100° C.). Comparative Examples C1-C3 use non-bridged metallocene compounds (Compounds X1 and X2), which resulted in high selectivity toward vinylidenes. However, the conversion of the monomer in these comparative examples tend to be very low. Comparative Examples C4, C5, C7, C8, and C9 use metallocene compounds that resulted in high selectivity toward 1,2-di-substituted vinylenes at the expense of vinylidenes and tri-substituted vinylenes. Comparative Example C6 showed high selectivity toward vinylidenes, but the conversion is too low, much lower than the conversion in the inventive examples. All of the metallocene compounds used in these comparative examples do not have the structure features of the metallocene of the present disclosure.

The data also shows how the use of different activation chemistries leads to differences in termination routes. And depending on the type of unsaturation desired, one can tailor the oligomerization process by use of various activators.

TABLE II

| Example No. | | Polymerization Conditions | | | Olefins | | | | Con (%) |
|---|---|---|---|---|---|---|---|---|---|
| | | MC | Activator | Temp (° C.) | Di | Tri | Vi | Vd | |
| 1 | a | I-1 | D4 | 60 | 2 | 5 | — | 94 | 16 |
| | b | | | 85 | 2 | 11 | — | 87 | 29 |
| | c | | | 110 | 3 | 17 | — | 81 | 49 |
| 2 | a | I-2 | D4 | 60 | 0 | 7 | — | 93 | 34 |
| | b | | | 85 | 0 | 12 | — | 88 | 46 |
| | c | | | 110 | 0 | 18 | — | 82 | 42 |
| 3 | a | I-3 | D4 | 60 | 4 | 7 | — | 89 | 58.0 |
| | b | | | 85 | 3 | 9 | — | 88 | 72.3 |
| | c | | | 110 | 4 | 13 | — | 83 | 73.1 |
| 4 | a | I-4 | D4 | 60 | 3 | 4 | — | 93 | 49.0 |
| | b | | | 85 | 3 | 9 | — | 88 | 69.5 |
| | c | | | 110 | 4 | 13 | — | 86 | 77.3 |
| 5 | a | I-5 | MAO | 60 | 6 | 8 | — | 85 | 26.9 |
| | b | | | 85 | 6 | 9 | — | 85 | 57.6 |
| | c | | | 110 | 7 | 13 | — | 80 | 56.9 |
| 6 | a | I-6 | D4 | 60 | 11 | 25 | — | 64 | 3.7 |
| | b | | | 85 | 6 | 36 | — | 58 | 4.2 |
| | c | | | 110 | 4 | 27 | — | 69 | 2.5 |
| 7 | a | I-7 | D4 | 60 | 1.9 | 12.7 | 10.2 | 75.2 | 69.1 |
| | b | | | 85 | 1.1 | 13.8 | 10.1 | 74.9 | 67.1 |
| | c | | | 110 | 0 | 10.8 | 9.6 | 79.6 | 56.8 |

MC: Metallocene compound
Temp: Polymerization temperature
Di: 1,2-di-substituted vinylenes
Tri: Tri-substituted vinylenes
Vi: Vinyls
Vd: Vinylidenes
Con: Conversion

TABLE III

| Example No. | | Polymerization Conditions | | | Olefins | | | | Con (%) |
|---|---|---|---|---|---|---|---|---|---|
| | | MC | Activator | Temp (° C.) | Di | Tri | Vi | Vd | |
| C1 | a | X-1 | D4 | 60 | 5.4 | 17.1 | — | 77.5 | 7.9 |
| | b | | | 85 | 4.6 | 18.5 | — | 76.9 | 12.8 |
| | c | | | 110 | 4.8 | 20.8 | — | 74.3 | 18.0 |
| C2 | a | X-2 | D4 | 60 | 6.8 | 8.5 | — | 84.7 | 18.7 |
| | b | | | 85 | 4.3 | 10.2 | — | 85.5 | 17.5 |
| | c | | | 110 | 4.9 | 12.8 | — | 82.3 | 59.0 |
| C3 | a | X-2 | D9 | 60 | 7.7 | 6.8 | — | 85.5 | 17.7 |
| | b | | | 85 | 6.7 | 10.0 | — | 83.3 | 44.4 |
| | c | | | 110 | 6.6 | 11.5 | — | 82.0 | 54.9 |
| C4 | a | X-3 | D4 | 60 | 21 | 12 | — | 66 | 8.6 |
| | b | | | 85 | 11 | 11 | — | 79 | 37.9 |
| | c | | | 110 | 6 | 13 | — | 80 | 65.6 |
| C5 | a | X-3 | MAO | 60 | 25 | 4 | — | 72 | 7 |
| | b | | | 85 | 16 | 9 | — | 75 | 35 |
| | c | | | 110 | 12 | 12 | — | 75 | 26 |
| C6 | a | X-4 | MAO | 60 | 5 | 6 | — | 89 | 8 |
| | b | | | 85 | 7 | 8 | — | 86 | 8 |
| | c | | | 110 | 10 | 10 | — | 79 | 5 |
| C7 | a | X-5 | D4 | 60 | 14 | 25 | — | 61 | 66.4 |
| | b | | | 85 | 11 | 28 | — | 61 | 78.0 |
| | c | | | 110 | 10 | 27 | — | 63 | 52.7 |
| C8 | a | X-6 | MAO | 60 | 67 | — | — | 33 | 52.3 |
| | b | | | 85 | 81 | — | — | 19 | 67.4 |
| | c | | | 110 | 83 | — | — | 17 | 60.8 |
| C9 | a | X-7 | D4 | 60 | 13 | 9 | — | 79 | 72 |
| | b | | | 85 | 12 | 12 | — | 75 | 84 |
| | c | | | 110 | 15 | 18 | — | 68 | 84 |

MC: Metallocene compound
Temp: Polymerization temperature
Di: 1,2-di-substituted vinylenes
Tri: Tri-substituted vinylenes
Vi: Vinyls
Vd: Vinylidenes
Con: Conversion

What is claimed is:

1. A process for making a polyalpha-olefin ("PAO"), the process comprising:

contacting a C6-C30 alpha-olefin feed with a catalyst system comprising a metallocene compound in a polymerization reactor under polymerization conditions in the absence of hydrogen to effect a polymerization reaction to obtain a polymerization reaction mixture comprising vinylidenes, tri-substituted vinylenes, optionally 1,2-di-substituted vinylenes, and optionally vinyls; and obtaining an unsaturated PAO product from the polymerization reaction mixture, wherein the unsaturated PAO product comprising, based on the total moles of vinyls, vinylidenes, 1,2-di-substituted vinylenes, and tri-substituted vinylenes contained therein:

80 to 90 mol % of vinylidenes;

0.1 to 10 mol % of 1,2-di-substituted vinylenes; and 0 to 10 mol % of vinyls, based on the total moles of vinyls, vinylidenes, 1,2-di-substituted vinylenes, and tri-substituted vinylenes contained therein, wherein:

the metallocene compound has a structure represented by formula (F-MC) below comprising a first cyclopentadienyl ring directly connected with $R^1$, $R^2$, $R^3$, and $R^4$ and a second cyclopentadienyl ring directly connected with $R^5$, $R^6$, $R^7$, and $R^8$:

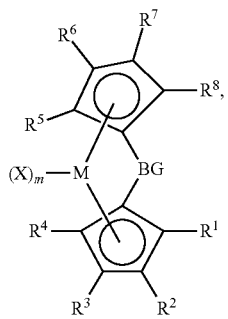

(F-MC)

wherein:
$R^1$ and $R^4$ are each independently a hydrogen, a substituted or unsubstituted linear, branched linear, or cyclic C1-C30 hydrocarbyl group,
$R^2$ and $R^3$ are each independently a substituted or unsubstituted linear, branched linear, or cyclic C1-C50 hydrocarbyl group, or
alternatively, two or more of $R^1$, $R^2$, $R^3$, and $R^4$, taken together, with the carbon atoms in the first cyclopentadienyl ring to which they are directly connected, form one or more substituted or unsubstituted ring annelated to the first cyclopentadienyl ring;
$R^5$, $R^6$, $R^7$, and $R^8$ are each independently a hydrogen, or a substituted or unsubstituted linear, branched linear, or cyclic C1-C30 hydrocarbyl group, provided: $R^6$ and $R^7$ are not both hydrogen; or
alternatively, two or more of $R^5$, $R^6$, $R^7$, and $R^8$, taken together, with the intermediate carbon atoms in the second cyclopentadienyl ring to which they are directly connected, form one or more substituted or unsubstituted ring annelated to the second cyclopentadienyl ring;
provided: the first cyclopentadienyl ring and the second cyclopentadienyl ring are not annelated to ring structures simultaneously;
BG is a bridging group connected directly with both the first cyclopentadienyl ring and the second cyclopentadienyl ring;
M is a transition metal having a valency of v;
X, the same or different at each occurrence, is independently selected from halogens, C1-C50 substituted or unsubstituted linear, branched, or cyclic hydrocarbyl groups; and
m is an integer equal to v-2.

2. The process of claim 1, wherein M is selected from Ti, Zr, or Hf.

3. The process of claim 1, wherein:
the polymerization reaction exhibits a selectivity toward 1,2-di-substituted vinylenes of at most 3%.

4. The process of claim 1, wherein:
$R^1$ and $R^4$ are each independently a substituted or unsubstituted linear, branched linear, or cyclic C1-C30 hydrocarbyl group.

5. The process of claim 1, wherein:
at least one of $R^5$ and $R^8$ is hydrogen.

6. The process of claim 4, wherein:
the polymerization reaction exhibits a selectivity toward vinyls of at most 5%.

7. The process of claim 1, wherein:
both $R^5$ and $R^8$ are each independently substituted or unsubstituted linear, branched linear, or cyclic C1-C50 hydrocarbyl group.

8. The process of claim 1, wherein the bridging group -BG- is selected from

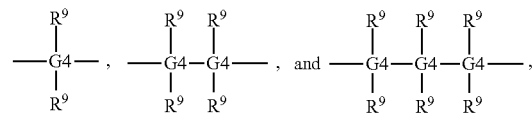

where G4 are, the same or different at each occurrence, independently selected from carbon, silicon, or germanium, or groups $R^9$, the same or different at each occurrence, are each independently a C1-C30 substituted or unsubstituted linear, branched, or cyclic hydrocarbyl groups.

9. The process of claim 8, wherein:
-BG- is selected from

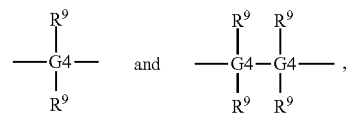

where $R^9$ is selected from methyl, ethyl, benzyl, and halogen.

10. The process of claim 1, wherein
M is selected from Zr and Hf;
X is independently selected from methyl, ethyl, benzyl, and halogen; and
m is 2.

11. The process of claim 1, wherein the catalyst system further comprises a non-coordinating anion type activator.

12. The process of claim 1, wherein:
the metallocene compound is selected from the following compounds I-1 to I-13, optical isomers of the following compounds I-1 to I-13, or combinations thereof:

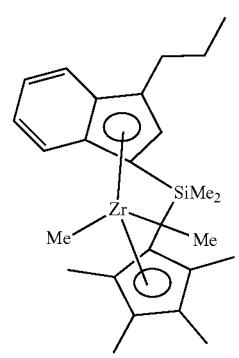

I-1

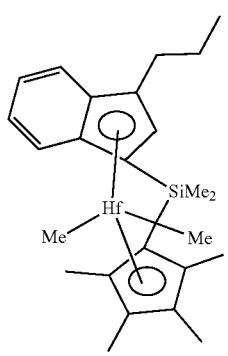
I-2
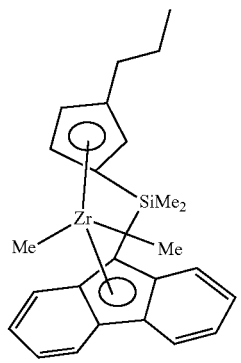
I-6
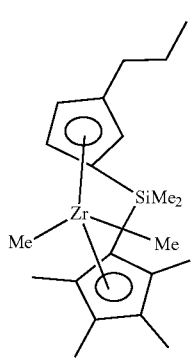
I-3
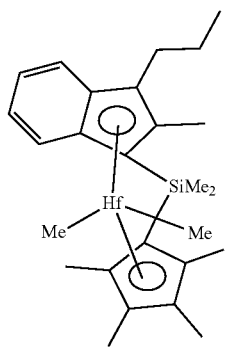
I-7
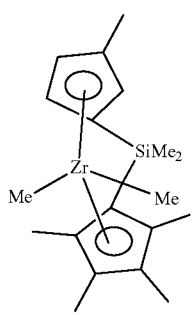
I-4
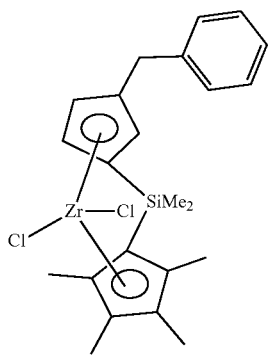
I-8
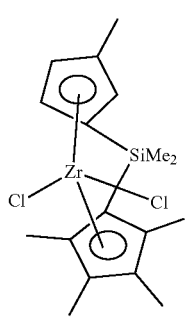
I-5
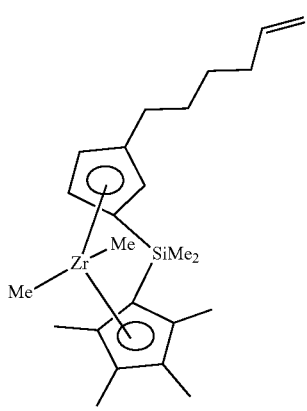
I-9

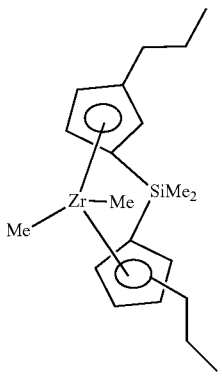

I-10

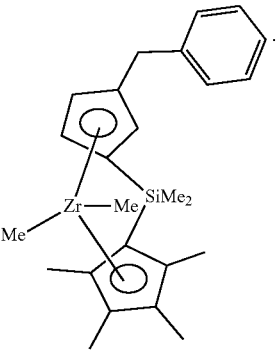

I-13

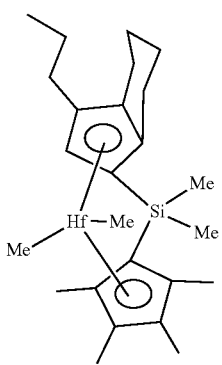

I-11

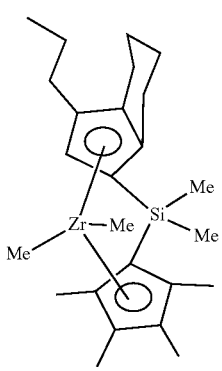

I-12

13. The process of claim 1, further comprising:
contacting the unsaturated PAO product with hydrogen to convert at least a portion of the unsaturated PAO product to a hydrogenated PAO product.

14. An unsaturated polyalpha-olefin ("PAO") product obtained by an oligomerization reaction of one or more C6-C30 alpha-olefin monomers in the absence of hydrogen, the product comprising, based on the total moles of vinyls, vinylidenes, 1,2-di-substituted vinylenes, and tri-substituted vinylenes contained therein:
80 to 90 mol % of vinylidenes;
0.1 to 10 mol % of 1,2-di-substituted vinylenes; and
0 to 10 mol % of vinyls, based on the total moles of vinyls, vinylidenes, 1,2-di-substituted vinylenes, and tri-substituted vinylenes contained therein.

15. The unsaturated PAO product of claim 14, comprising, based on the total moles of vinyls, vinylidenes, 1,2-di-substituted vinylenes, and tri-substituted vinylenes contained therein:
at most 5% of 1,2-di-substituted vinylenes; and
at most 5% of vinyls.

16. The unsaturated PAO product of claim 14, comprising, based on the total moles of vinyls, vinylidenes, 1,2-disubstituted vinylenes, and tri-substituted vinylenes contained therein:
at least 90 mol % of vinylidenes and tri-substituted vinylenes combined.

17. A partially saturated or substantially all saturated polyalpha-olefins product, obtained by hydrogenating the unsaturated PAO product of claim 14.

18. A partially saturated or substantially all saturated polyalpha-olefins product, obtainable by hydrogenating the unsaturated PAO product of claim 1.

19. The unsaturated PAO product of claim 16 comprising, based on the total moles of vinyls, vinylidenes, 1,2-disubstituted vinylenes, and tri-substituted vinylenes contained therein:
at most 3% of 1,2-di-substituted vinylenes.

* * * * *